United States Patent
Machuca et al.

(10) Patent No.: US 9,541,539 B2
(45) Date of Patent: Jan. 10, 2017

(54) DISSOLVED OXYGEN SENSOR

(71) Applicant: Entegris—Jetalon Solutions, Inc., Pleasant Hill, CA (US)

(72) Inventors: Francisco Javier Machuca, Oakland, CA (US); Kyle William Montgomery, Pleasanton, CA (US); Ronald Phillip Chiarello, Lafayette, CA (US)

(73) Assignee: Entegris, Inc., Billerica, MA (US)

( * ) Notice: Subject to any disclaimer, the term of this patent is extended or adjusted under 35 U.S.C. 154(b) by 0 days.

(21) Appl. No.: 14/529,504

(22) Filed: Oct. 31, 2014

(65) Prior Publication Data

US 2015/0125347 A1    May 7, 2015

Related U.S. Application Data

(60) Provisional application No. 61/898,906, filed on Nov. 1, 2013, provisional application No. 61/899,605, filed
(Continued)

(51) Int. Cl.
  *G01N 21/77*  (2006.01)
  *G01N 21/64*  (2006.01)
  (Continued)

(52) U.S. Cl.
  CPC .......... *G01N 33/18* (2013.01); *G01N 21/643* (2013.01); *G01N 21/6408* (2013.01);
  (Continued)

(58) Field of Classification Search
  None
  See application file for complete search history.

(56) References Cited

U.S. PATENT DOCUMENTS 4,892,383 A * 1/1990 Klainer et al. .................. 385/12
5,272,090 A  12/1993 Gavish et al.
(Continued)

FOREIGN PATENT DOCUMENTS

CA      2869265 A1   10/2013
CN   202110139 U    1/2012
(Continued)

OTHER PUBLICATIONS

International Search Report and Written Opinion for International Application No. PCT/US2015/021586, mailed Jun. 12, 2015, 14 pgs.
(Continued)

*Primary Examiner* — Neil N Turk
(74) *Attorney, Agent, or Firm* — Sprinkle IP Law Group

(57) ABSTRACT

Embodiments of a dissolved oxygen sensor are disclosed herein. Embodiments as disclosed herein may include a window of optically transparent material disposed in an opening in a fluid flow path, where a luminophor is attached to the side of the window exposed to the fluid in the flow path. An optical probe may be disposed opposite the window from the fluid flow path on an axis at an angle to the window fluid flow path. The optical probe includes an excitation light source for illumination of the luminophor and a reference light source. An optical reception guide is configured to conduct light from the luminophor to a photodiode adjacent to the end of the optical reception guide distal the window when the luminophor is illuminated by the excitation light source. The optical probe is configured to determine a measure of oxygen concentration of the fluid in the flow path. The optical reception guide and photodiode may be aligned on axis, where the axis may be substantially parallel with the axis on which the optical probe is aligned.

18 Claims, 13 Drawing Sheets

Related U.S. Application Data on Nov. 4, 2013, provisional application No. 61/955,966, filed on Mar. 20, 2014.

(51) Int. Cl.
*G01N 33/18* (2006.01)
*G01N 21/85* (2006.01)
*G01N 27/404* (2006.01)
*A61B 5/083* (2006.01)

(52) U.S. Cl.
CPC ............ *G01N 21/77* (2013.01); *G01N 21/85* (2013.01); *G01N 33/1806* (2013.01); *A61B 5/0833* (2013.01); *G01N 2021/6432* (2013.01); *G01N 2021/7786* (2013.01)

(56) References Cited

U.S. PATENT DOCUMENTS

| | | | |
|---|---|---|---|
| 6,664,111 | B2 | 12/2003 | Bentsen et al. |
| 7,916,285 | B2 | 3/2011 | Amamiya et al. |
| 2001/0031224 | A1* | 10/2001 | Labuda et al. ................. 422/84 |
| 2006/0257094 | A1 | 11/2006 | McEvoy et al. |
| 2008/0085217 | A1 | 4/2008 | Mueller |
| 2013/0023782 | A1 | 1/2013 | Karlsson |
| 2013/0036799 | A1* | 2/2013 | Silveri .......................... 73/61.41 |

FOREIGN PATENT DOCUMENTS

| | | |
|---|---|---|
| JP | 2003004635 | 1/2003 |
| WO | WO2012078327 | 6/2012 |

OTHER PUBLICATIONS

International Search Report and Written Opinion for International Application No. PCT/US2014/063329, mailed Feb. 3, 2015, 5 pgs.

Weigl, Bernard H. et al., "Optical Triple Sensor for Measuring pH, Oxygen and Carbon Dioxide," Journal of Biotechnology, vol. 32, No. 2, Copyright 1994 by Elsevier Science Publishers, 12 pages.

2nd Written Opinion issued for PCT Application No. PCT/US2014/063329, mailed Sep. 29, 2015, 5 pages.

International Preliminary Report on Patentability issued for PCT Application No. PCT/US2014/063329, mailed Jan. 15, 2016, 18 pages.

\* cited by examiner

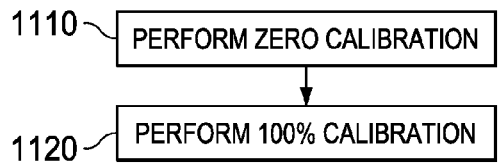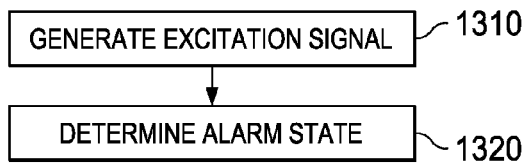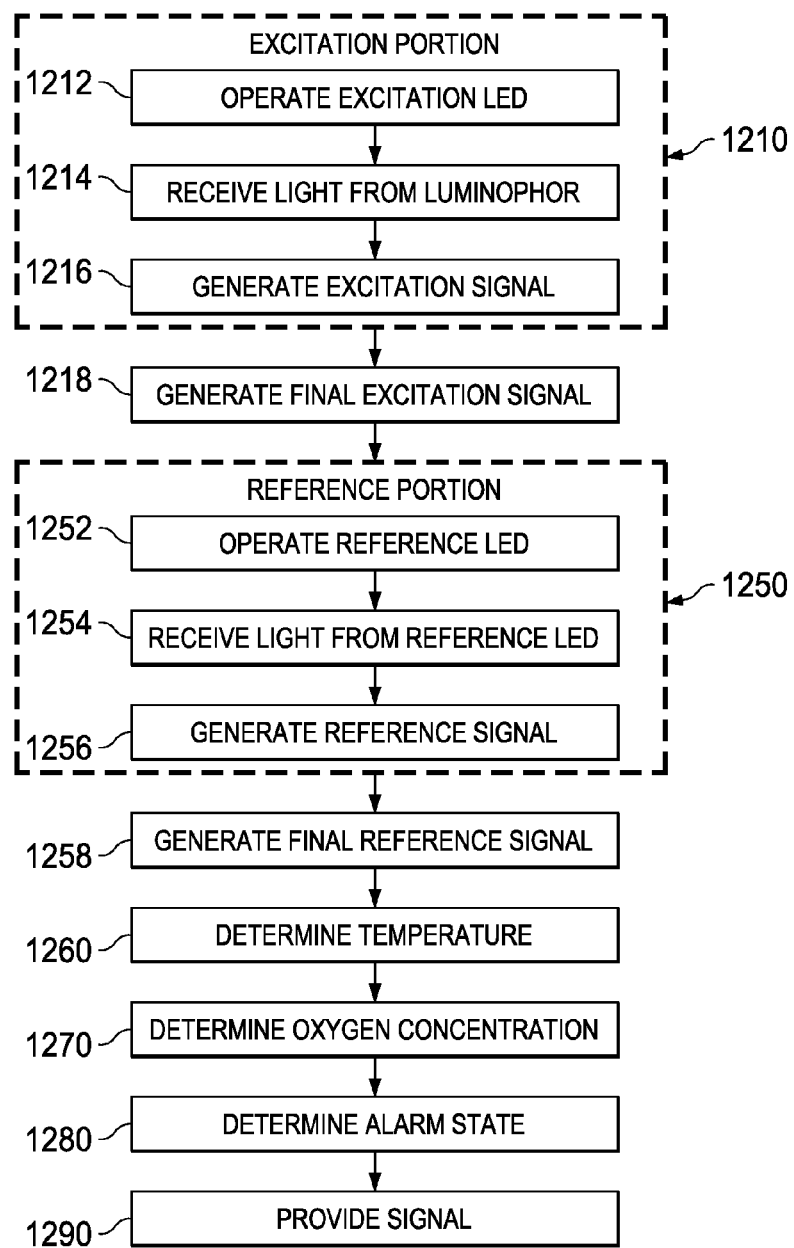
FIG. 11
FIG. 13
FIG. 12

DISSOLVED OXYGEN SENSOR

RELATED APPLICATIONS

This patent application claims a benefit of priority under 35 U.S.C. §119 to U.S. Provisional Patent Application Ser. No. 61/898,906 filed Nov. 1, 2013, entitled "Device And Method To Measure Sub Part Per Billion Concentration Of Dissolved Oxygen In Liquids"; U.S. Provisional Patent Application Ser. No. 61/899,605 filed Nov. 4, 2013, entitled "Device And Method To Measure the Concentration Of Dissolved Oxygen In Liquid"; and U.S. Provisional Patent Application Ser. No. 61/955,966 filed Mar. 20, 2014, entitled "Dissolved Oxygen Sensor And Auto-Detect End Of Life Of Light-Emitting Substance", all of which are incorporated herein in their entirety by reference for all purposes.

TECHNICAL FIELD

This disclosure relates generally to oxygen sensors. More particularly, this disclosure relates to dissolved oxygen (DO) sensors. Even more specifically, this disclosure relates to sensitive, miniaturized DO sensors suitable for ultra-high purity environments.

BACKGROUND

An oxygen sensor refers to an electronic device that measures the concentration of oxygen in aqueous solutions in the field or in the laboratory. Currently, the most prevalent type of oxygen sensors are electrochemical sensors such as those used to measure oxygen concentration for determining environmental properties of large bodies of water to ensure appropriate environmental conditions for wildlife. These electrochemical sensors use a probe with electrodes to measure oxygen dissolved in a fluid. More specifically, a cathode and an anode are submersed in an electrolyte. Oxygen enters the probe through a permeable membrane by diffusion, and is reduced at the cathode, creating a measurable electrical current. The relationship between the electrical current and the oxygen concentration is a linear one and thus concentration can be determined from the current and calibration settings for the sensor.

There is, however, a need for oxygen sensors in other environments. In particular, there is a need for oxygen sensors in ultra-high purity environments such as those defined by SEMI F57 standard, FDA standards in food and drug processing or the like. This need arises for a variety of reasons. For example, the presence of oxygen in semiconductor manufacturing processing may increase corrosion of materials involved in the process (e.g., copper used in a plating process) among other problems.

Attempts to adapt electromechanical sensors to ultra-high purity environments has proved well-nigh impossible because it is extremely difficult to re-purpose electrochemical sensors that use relatively large metal probes (e.g., stainless steel or aluminum) originally intended as dip probes to sample dissolved oxygen content in rivers, streams, and lakes to ensure minimum oxygen concentrations levels for wildlife to the task of detecting the sub-part per billion (e.g., 1 part in $10^9$) concentrations of oxygen required for use in semiconductor manufacturing processes, food and drug processes, or other ultra-high purity environments. From an industry perspective such attempts have heretofore been failures.

This failure is due in no small part to the very nature of electrochemical sensors. As discussed above, electrochemical sensors use metal probes (or metal housings) that must be inserted in the fluid being measured. The insertion of these metal probe tips, for example in the process fluid of a semiconductor manufacturing process, serves to contaminate the process fluid in which it is inserted, making the use of such electrochemical sensors incompatible with the materials and processes in which they are being utilized and the standards for those processes. As such electrochemical sensors cannot be used with the caustic fluids that may be utilized in these ultra-high purity environments. In other words, there may a fundamental materials incompatibility between the materials of such electro chemical sensors and the fluids used in ultra-high purity environments that prevents adherence to standards that define those environments.

Moreover, the presence of the probe tips of electrochemical sensors in the fluid serves to disrupt the laminar flow of the fluid, agitating the fluid and causing dead legs in the fluid flow path. These disruptions may, in turn, cause unwanted side effects such as bubbles, or variations in dispense rates, etc. that negatively affect the process in which the fluid is being utilized. Other problems with the use of these electrochemical sensors include the fact that electrochemical sensors may have a relatively large form factor and be ill-designed for use in the high pressure flow rates that are sometimes utilized in ultra-high purity environments. Thus, in many cases, such electrochemical sensors may not be used at all in the compact installations sometimes utilized in ultra-high purity environments or may experience a high rate of failure due to leakage or corrosion resulting from poor internal sealing.

What is desired then, are oxygen sensors suitable for use in ultra-high purity environments. In particular, compact oxygen sensors having a small footprint that are also suitable for use in ultra-high purity environments are desired.

SUMMARY OF THE DISCLOSURE

To that end, embodiments of a dissolved oxygen sensor are disclosed herein. Embodiments as disclosed herein may include a window of optically transparent material disposed in an opening in a fluid flow path, where a luminophor is attached to the side of the window exposed to the fluid in the flow path. An optical probe may be disposed opposite the window from the fluid flow path on an axis at an angle to the window fluid flow path. The optical probe includes an excitation light source for illumination of the luminophor and a reference light source. An optical reception guide is configured to conduct light from the luminophor to a photodiode adjacent to the end of the optical reception guide distal the window when the luminophor is illuminated by the excitation light source. The optical probe also includes a printed circuit board (PCB) containing electronic components configured to determine a measure of oxygen concentration of the fluid in the flow path. The optical reception guide, photodiode and PCB may be aligned on an axis, where in some embodiments the axis may be substantially parallel with the axis on which on which the optical probe is aligned.

By aligning these components the size or footprint of the sensor may be reduced while sensitivity is maintained. In particular, the arrangement of the components of dissolved oxygen sensors according to embodiments herein allows such oxygen sensors to be both compact and suitable for use in ultra-high purity environments. More specifically, by aligning the components of the optical probe, including the optical reception guide, photodiode, reference light source and PCB, the footprint of the sensor may be reduced.

Moreover, the use of an optical carrier that allows optical and electrical separation of the excitation light source from the reference light source while allowing an optical reception guide and optical transmission guide to share at least a portion of the same path through the optical probe may also contribute to a sensor with a small footprint or otherwise reduced size. By achieving a sensor with reduced size and ultra-high purity compatibility, embodiments of such a sensor may be suitable for use in a wide variety of process where previously DO sensors were unable to be utilized or did not meet the performance or serviceability desires of operators of those processes.

Additionally by configuring these embodiments such that no portion of the optical probe is within the fluid flow path, the fluid flow path may be scaled to substantially any desired diameter while still maintaining laminar flow increasing the environments in which such a sensor may be utilized. Moreover, as only the window of such a sensor may be in contact with the fluid, electronic and other components of the sensor may be effectively sealed against fluid intrusion, extending the lifetime of the sensor in a harsh environment, in which caustic and molecularly small chemicals may be used.

In certain embodiments, the window utilized may be high strength, optically transparent material that exhibits a high degree of thermal conductivity such as sapphire or diamond. By using such materials for the window a high degree of sealing force may be utilized. To apply such a sealing force an annular retainer or retainer nut may be utilized in certain embodiments. Such an annular retainer nut may be threaded around its outer circumferences such that it can be screwed into a threaded wall of a body of the sensor above the window. The tip of the optical probe can reside or otherwise be disposed in the center of the retainer nut such that it is held a working distance from the window. The use of such a retainer or retainer nut may allow easy replacement of the luminophor (e.g., easy removal of the window without having to touch or remove any components within the optical probe itself), increasing the field serviceability of such a sensor and reducing expense by reducing process downtimes.

In conjunction with such serviceability and cost reduction goals, embodiments of the sensor may provide an indicator when the luminophor may need replacement. In particular, in certain embodiments the magnitude of light emitted by the luminophor may be monitored to determine if the luminophor should be replaced. In this manner, accurate functioning of dissolved oxygen (DO) sensor may be maintained while avoiding the unnecessary expense of frequent luminophor replacement. More specifically, a baseline magnitude for the luminophor may be determined and stored with respect to the DO sensor. This baseline magnitude may be an absolute value that may be user determined and set or may be determined during a calibration process and may be indicative of the maximum intensity of light emitted by the luminophor. During a measurement cycle (which may be every measurement cycle, a designated measurement cycle performed under certain conditions, etc.) a magnitude of the light emitted by the luminophor may be determined and compared to this baseline magnitude. If the determined magnitude for the light emitted by the luminophor during that measurement cycle is not within some threshold of the baseline magnitude an alarm may be generated. This alarm may signal operators (e.g., of a process) employing such a DO sensor that the luminophor of the sensor needs replacement and operators may take a wide variety of actions based on the alarm, including shutting down a process, replacing the luminophor, etc.

To increase the sensitivity or accuracy of embodiments of such a sensor the optical probe may separate certain functionality or components to prevent electrical optical crosstalk. In particular, according to certain embodiments, the optical probe may include an optical carrier disposed within an optical sleeve. The excitation light source of the DO sensor may be on one side of the optical carrier while the reference light source, photodiode and optical reception carrier configured to conduct light emitted by luminophor to the photodiode may be separated from the excitation light, by placing these components on the other side of the optical carrier or by encasing them in various chambers or bores of the optical carrier. Thus, the combination of the optical carrier (and the components thereon) and the optical sleeve encasing the optical carrier serves to electrically and optically isolate the components of the sensor.

These, and other, aspects of the invention will be better appreciated and understood when considered in conjunction with the following description and the accompanying drawings. The following description, while indicating various embodiments of the invention and numerous specific details thereof, is given by way of illustration and not of limitation. Many substitutions, modifications, additions or rearrangements may be made within the scope of the invention, and the invention includes all such substitutions, modifications, additions or rearrangements.

BRIEF DESCRIPTION OF THE DRAWINGS

A more complete understanding of the present invention and the advantages thereof may be acquired by referring to the following description, taken in conjunction with the accompanying drawings in which like reference numbers indicate like features and wherein:

FIG. 11 is a flow diagram for one embodiment of a calibration process used to control embodiments of a DO sensor;

FIG. 12 is a flow diagram for one embodiment of a measurement process used to control embodiments of a DO sensor; and FIG. 13 is a diagrammatic representation of a view of one embodiment of an alarm state determination process used to control embodiments of a DO sensor.

DETAILED DESCRIPTION

The disclosure and the various features and advantageous details thereof are explained more fully with reference to the non-limiting embodiments that are illustrated in the accompanying drawings and detailed in the following description. Descriptions of well-known starting materials, processing techniques, components and equipment are omitted so as not to unnecessarily obscure the disclosure in detail. Skilled artisans should understand, however, that the detailed description and the specific examples, while disclosing preferred embodiments, are given by way of illustration only and not by way of limitation. Various substitutions, modifications, additions or rearrangements within the scope of the underlying inventive concept(s) will become apparent to those skilled in the art after reading this disclosure. As an example, it should be noted that embodiments as described herein relate to a dissolved oxygen sensor, however, other embodiments may equally well be utilized to measure the concentration of other chemicals or elements, by for example, using a luminophor responsive to other elements or molecules (e.g., carbon dioxide).

Figure 1:
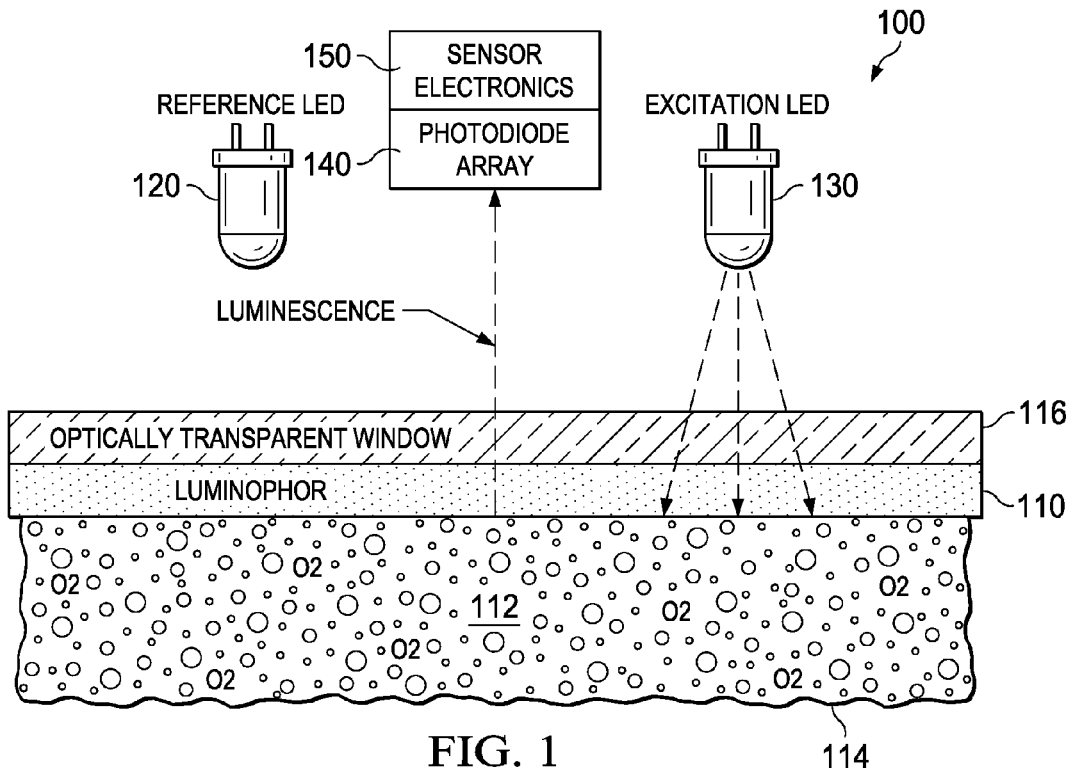
FIG. 1 is a diagrammatic representation of one embodiment of the functioning of a dissolved oxygen (DO) sensor.

Before delving into more detail regarding particular embodiments of oxygen sensors, it will be helpful to give an overview of the general operation of embodiments and the context in which such embodiments may be utilized. Turning first to FIG. 1 then, the basic operation of embodiments of an optical dissolved oxygen (DO) sensor is illustrated. Optical sensors use fluorescence optical techniques to take optical measurements of the oxygen concentration. Specifically, a chemical film which has fluorescence properties that depend on the oxygen concentration of a fluid may be utilized. Unlike the measurable electrical current created by electrochemical sensors, the signal (fluorescence) to oxygen ratio for optical sensors may not be linear. Fluorescence is at a maximum when there is no oxygen present. When an oxygen molecule ($O_2$) comes along, it collides with the film and this quenches the photoluminescence. Accordingly, the sensitivity decreases as oxygen concentration increases. This is known as a photophysical intermolecular deactivation (quenching) process. An intermolecular deactivation is where the presence of another chemical species can accelerate the decay rate of a chemical in its excited state. Processes such as fluorescence and phosphorescence are examples of excited state processes which can be quenched.

DO monitor 100 includes luminophor 110 that is interfaced with fluid 112 (e.g., a liquid or gas) flowing through a fluid flow path 114. For example, DO sensor 100 may include a housing that includes a flow path 114 or may otherwise be interfaced with, or attached to, an existing fluid flow path, through for example a physical coupling. DO sensor 100 may serve to measure the concentration of oxygen present in the fluid 112 as it flows through the flow path 114 using luminophor 110.

Luminophor 110 utilizes a fluorescing material including atoms or an atomic grouping that when present in a substance such as a chemical compound or organic compound increases the ability of the substance to emit light (luminescence). As shown in FIG. 1, the light emitting (fluorescing) substance comprising the luminophor material 110 is adhered or otherwise joined to an optically transparent window 116 (e.g., a high purity sapphire substrate, diamond, synthetic diamond, borosilicate glass, etc.) and is in contact with fluid 112 exhibiting some level of dissolved oxygen. In some embodiments, the fluorescing material, is, or can be coated, or used in conjunction with, a thin organic or inorganic film (e.g., a high performance resistive coating such a ceramic coating or the like) that is impervious to strong acid or base attack, but allows oxygen to freely diffuse and make contact with the fluorescing material of the luminophor 110, enabling use of the luminophor 110 with caustic fluids such as those used in wet etch chemistry or the like.

After being excited by an excitation light source 130 such as an LED (e.g., red green, blue, etc.), the light emitting substance of the luminophor 110 emits light by luminescence which is optically guided into a light detecting photodiode 140 positioned to receive light emitted from the luminophor 110 through the optically transparent window 116. A reference light source 120 such as an LED, may emit light that may be detected by photodiode 140 to create a reference signal that can be used to remove system errors or delays or allow lock in phase detection methods to minimize noise and increase the signal to noise ratio.

Accordingly, during an excitation portion of a measurement cycle, the excitation light source 130 may be operated for a period of time and the light emitted by luminophor 110 received by photodiode 140. Photodiode 140 generates a signal based on this received light and provides this signal to sensor electronics 150. Sensor electronics 150 include some combination of hardware (e.g., a digital signal processor (DSP), microcontroller, analog to digital converter, etc.) and software (e.g., firmware or the like) that is configured to generate a corresponding signal based on the signal received from photodiode 140. In this case, sensor electronics 150 generate an excitation signal based on the signal from the photodiode 140 during the excitation portions. This excitation signal corresponds, for example, to the magnitude or phase of the light received through photodiode 140 as emitted by luminophor 110 in response to illumination by excitation light source 130 which is, as noted above, based on the concentration of oxygen in fluid 112.

During a reference portion of the measurement cycle the reference light source 120 may be operated for a period of time and the light emitted by this reference light source 120 received by photodiode 140. Photodiode 140 generates a signal based on this light received from reference light source 120 and provides this signal to sensor electronics 150. Sensor electronics 150 generate a reference signal based on the signal received from the photodiode 140 during the reference portion of the measurement cycle. This reference signal corresponds, for example, to the magnitude or phase of the light received through photodiode 140 as emitted by reference light source 120.

Sensor electronics 150 uses the excitation signal generated during the excitation portion of the measurement cycle to generate a signal indicating a measurement of the oxygen concentration of the fluid 112. Specifically, the amplitude or decay time of the light emitted by the luminophor 110 may have an inverse and linear relationship to the dissolved oxygen concentration in the fluid 112. Thus, the excitation signal may be used to derive a decay time or decay time constant corresponding to the decrease in fluorescence as dissolved oxygen in fluid 112 interacts with the fluorescing material of luminophor 110 to quench or decrease the amount of fluorescence of that material.

In particular, in certain embodiments, the phase of the excitation signal may be determined. Additionally, a delay in sensor electronics 150 may be determined, for example, using the reference signal (e.g., the phase of the reference signal) determined during the reference portion of the measurement cycle. The phase of the excitation signal can be used to accurately determine the decay time of the fluorescence of luminophor 110 during the excitation portion (e.g., using the signal used to operate the excitation light source 130 during the excitation portion). In determining this decay time, any delay in the sensor electronics may be corrected for using the delay determined from the reference signal. A measure of concentration of the oxygen in the fluid can then be determined based on relationship between the known decay time constant of luminophor 110 and the determined decay time. In some embodiments, this measure of concentration can be further adjusted using a measured temperature value using a known relationship between temperature and oxygen concentration. Concentration correction using a measure temperature value may allow substantially real-time compensation for fluid temperature transients or steady state changes.

As described luminescence of luminophor 110 is quenched when oxygen is raised from its ground state to its excited stated. This quenching process can accelerate the decay rate of the luminophor 110. Accordingly, DO sensors using luminophors require regular maintenance. Current best practices involve changing out luminophors either based on time or failure to operate. However, changing out luminophors based on time may unnecessarily cut short the useful lifetime of luminophors and changing out luminophors based on failure to operate may be risky or costly, particularly if a DO sensor that failed to operate due to luminophor decay is used in a high precision operation. It is costly not at least because luminophor 110 may be adhered to optically transparent window 116 and it is usually the case that they are manufactured as a single unit. Thus, it may be this single unit including both the window 116 and the luminophor 110 that is replaced.

Additionally, luminophor 110 may decay at different rate depending on the fluid(s) 112 with which DO sensor 100 is being utilized. In other words, fluids with higher concentration of oxygen may cause luminophor 110 to degrade more quickly. Accordingly, there is a need to determine when luminophor 110 should be replaced to ensure adequate functioning of DO sensor 100 while reducing expenses associated with frequent and unnecessary replacement of luminophor 110 (and in many cases, window 116 as well).

To address this issue, in some embodiment, a measure of luminophor 110 decay may be determined. Specifically, in certain embodiments, sensor electronics 150 may determine a magnitude of the excitation signal, which may correspond to the intensity of the emissions from luminophor 110 and thus reflective of the decay of luminophor 110. This magnitude can then be compared against a baseline magnitude (e.g., determined during a calibration process for DO sensor, an absolute magnitude such as a set value, or otherwise) associated with luminophor 110. A determination is then made by sensor electronics 150 whether the magnitude of the excitation signal is within some threshold of the baseline magnitude. If the excitation signal is not within some threshold (e.g., 50%, 75%, etc.) of the baseline magnitude an alarm may be generated to inform a user (e.g., an operator associated with an entity operating the DO sensor) that replacement of luminophor 110 may be needed.

Figure 2:
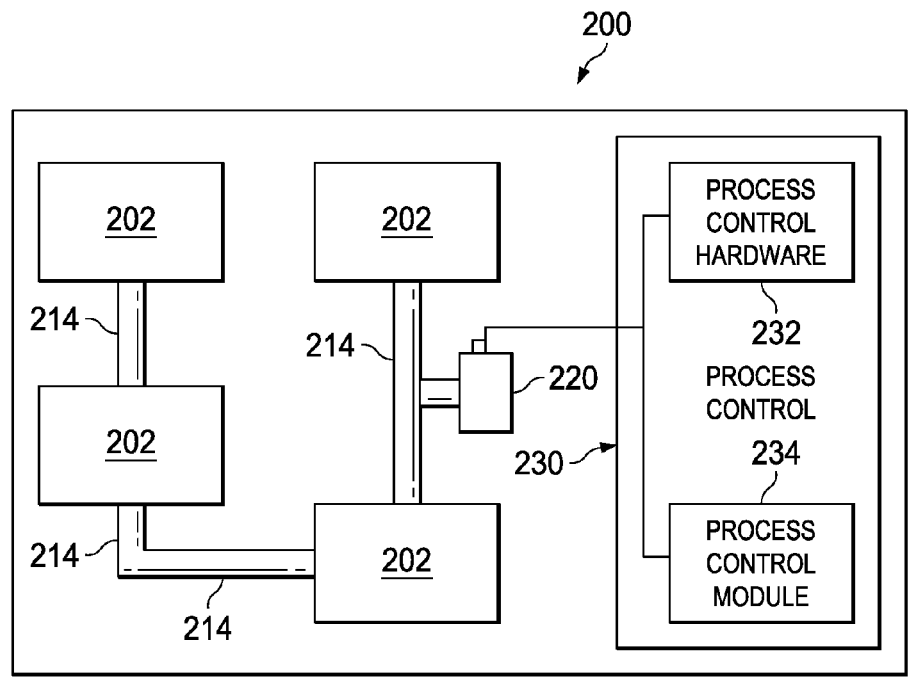
FIG. 2 is a diagrammatic representation of the use of a DO sensor in a semiconductor process.

Moving now to FIG. 2, a high level view of one embodiment of an operating environment for DO sensors as disclosed herein is illustrated. Such an operating environment may include a semiconductor process involved with the manufacturing of semiconductors as are known in the art, such as wet etch, photolithographic, plating or cleaning processes. Here, a semiconductor process 200 may include tools or chambers (collectively 202) and a fluid flow path 214 through which one or more fluids required in semiconductor process 200 is provided to the tools or chambers 202 used in the process 200. The semiconductor process 200 is controlled by process controller 230 which includes the digital hardware 232 (e.g., processors, storage devices, etc.) and modules 234 (control routines, software, etc.) used to control the semiconductor process 200, including for example, by operating various pumps, valves, tools or chambers 202, etc. to accomplish semiconductor process 200.

As discussed above, the presence of oxygen in the fluid(s) utilized in semiconductor process 200 may greatly affect the process 200. Thus, embodiments of a DO sensor 220 may be interfaced with, or into, fluid flow path 214 to measure the concentration of oxygen in the fluid being used in the semiconductor process 200 (e.g., a sample of the fluid in the portion of fluid flow path 214 adjacent, or contained in, DO sensor 220) and provide a concentration signal corresponding to that concentration of oxygen to process control computer 230 which may utilize the measure of oxygen as a variable in controlling the semiconductor process (e.g., may stop or alter the process 200, send an alert to operators of semiconductor process 200, etc.). Specifically, in certain embodiments, DO sensor may provide an analog signal between two values (e.g., 0 and 5 volts, 4-20 milliamps, etc.) to process control 230 and process control 230 may be calibrated or otherwise configured such that it can determine a value for the measure of concentration of oxygen from the signal provided by DO sensor 220.

Additionally, in some embodiments, DO sensor 220 may provide a signal corresponding to the temperature of the fluid in flow path 214 (e.g., the temperature of the sample of the fluid measured by DO sensor 220), and an alarm signal indicating if a luminophor of the DO sensor 220 needs replacement, to process control 230. In one embodiment, the temperature signal may be an analog signal (e.g., from 0 to 5 volts, 4-20 milliamps, etc.)) that is scalable while the alarm signal may be a binary analog signal (e.g., 0 volts may be indicative of an alarm signal indicating the luminophor needs replacement while 5 volts may be an "o.k." signal). It will be noted that the type of signal provided to process control 230 may be dependent on desires of operators of semiconductor process 200 or capabilities of process control 230 and that embodiments of DO sensor 220 may effectively utilize analog signals, digital signals or some combination as is desired.

As can be imagined, the use of DO sensors in such semiconductor process 200 is fraught with complications. Specifically, as has been discussed, in many cases, the fluids being utilized in semiconductor process 200 may be highly caustic while at the same time, the semiconductor process 200 itself may be highly susceptible to contamination. Thus, is it desired that a DO sensor 220 tolerate use in such harsh environments and be resistant to degradation caused by caustic and molecularly small chemicals while simultaneously having some (e.g., those in contact with the fluid) or all portions manufacturable from non-reactive plastic or polymer materials such as perfluoroalkoxy polymer (PFA), polypropylene (PP) and polytetrafluoroethylene (PTFE), polyvinylidene fluoride, polyvinylidene difluoride (PVDF), etc. that are compliant with ultra-high purity environments including for example, those mandated by SEMI F57 specifications or the like.

Besides these concerns, an additional concern related to the use of DO sensors in semiconductor process 200 is the size of the DO sensor 220 itself. In many cases, the use of large DO sensors in such semiconductor processes 200 is just not feasible (e.g., because of packaging or space concerns). Thus, it is desirable that DO sensors for use with semiconductor processes be as small as possible while still being accurate enough to detect the sub part per billion or part per million concentrations as need for use in such processes. Accordingly, the desired form factor and accuracy of these types of DO sensors may be make the packaging of the components of the DO sensors of high importance as well.

Figure 3:
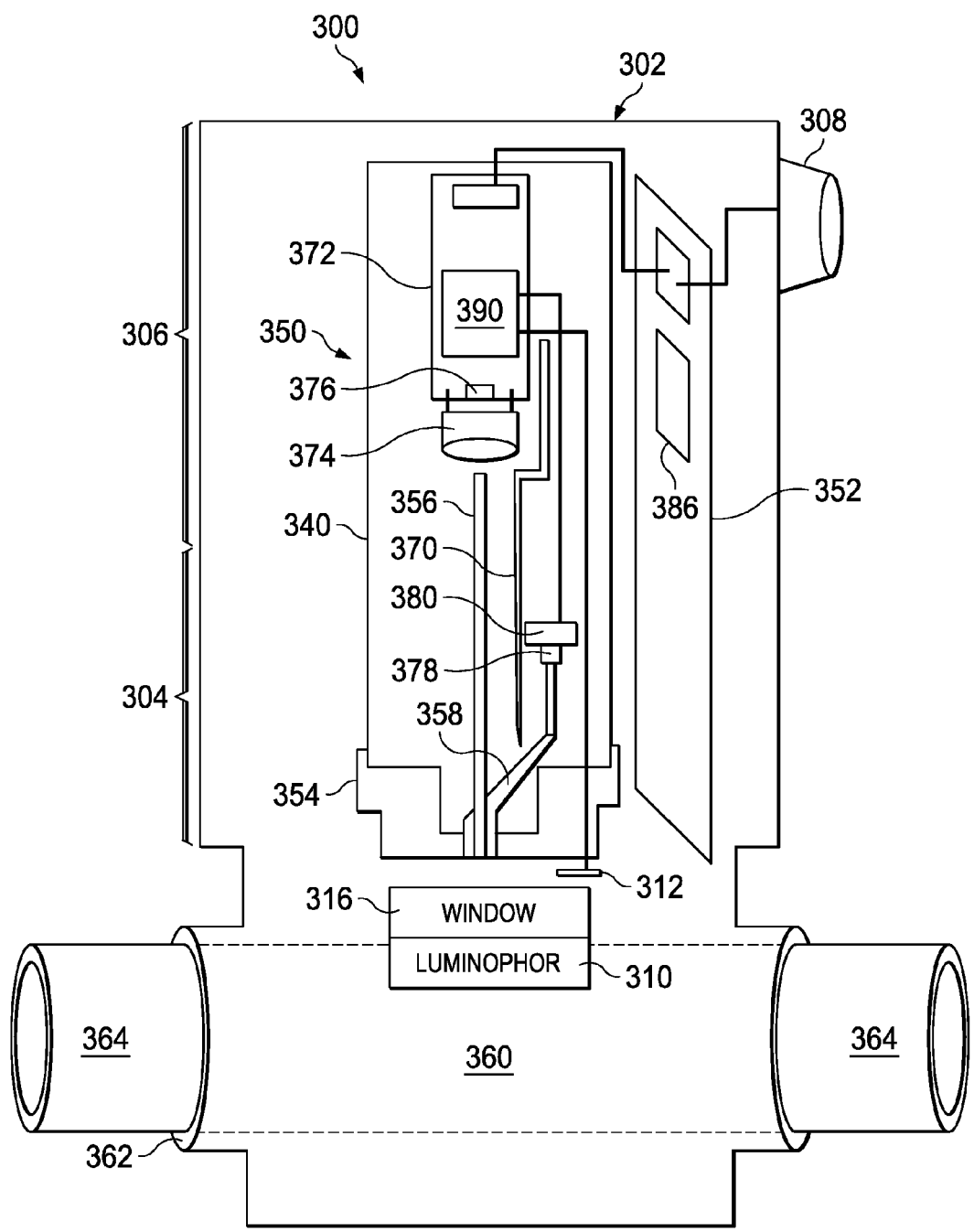
FIG. 3 is a diagrammatic representation of one embodiment of DO sensor.

FIG. 3 is a block diagram of one embodiment of a DO sensor that is small enough to be integrated into the majority of semiconductor processes while still achieving a desired level of sensitivity for use in semiconductor processes. DO sensor 300 in includes a housing 302, which may be formed, for example, out of plastic. A connector 308 for interfacing with, for example, process control systems or the like to provide signals (e.g., analog or digital) to the process control systems. This connector 308 may, for example, include one or more pins or pin outs conforming to the RS-232 protocol.

In certain embodiments, housing 302 may include an upper portion 306 and lower portion 304. Upper portion 306 may be joined to lower portion 304 using, for example, a gasket such that DO sensor is waterproof (e.g., IP67 compliant). To aid in water resistance, in some embodiments, components within housing 302 may also be potted or the like. Lower portion 304 of housing 302 includes, or is coupled to a body containing, a flow path 360 having ports 362 arranged for the ingress and egress of fluid from flow path 360. Fittings 364 connect ports 362 to other components such that the DO sensor 300 can be integrated (e.g., directly) into the fluid flow path of, for example, a semiconductor process or the like.

As DO sensor 300 may be integrated into a wide variety of processes which may comprise fluid flow paths of different diameters, embodiments of flow path 360 of DO sensor 300 may be appropriately sized to be integrated into such fluid paths, including for example ¼", ⅜", ½", ¾", and 1" diameter. Additionally, embodiments may have fittings 364 appropriate for the particular application in which the DO sensor 300 is to be utilized, including for example, Flaretek, PrimeLock, Nippon Pillar (e.g., S300) or another type of fitting Flow path 360 includes an opening through which an optically transparent window 316 having luminophor 310 adhered thereon may be exposed to fluid in flow path 360 such that fluid in flow path 360 directly contacts luminophor 310. In certain embodiments, luminophor 310 can be coated with a thin organic or inorganic film that is impervious or resistant to strong acid or base attack, but allows oxygen to freely in diffuse and make contact with the fluorescing film or material of luminophor 310. A temperature sensor 312 (such as a thermistor, thermocouple or the like) may be mounted to window 316 opposite the fluid flow path 360, using for example, an adhesive or other fastener.

Window 316 may be made of an optically transparent dielectric material such as borosilicate glass, sapphire, diamond, diamond coated glass, quartz, calcite, cubic zirconium, etc. As the thermo-conductivity of sapphire or diamond is relatively high (e.g., compared to borosilicate glass, etc.), certain embodiments may utilize sapphire or diamond for window 316 to allow temperature sensor 312 to have a greater sensitivity despite that the sensor 312 may reside outside the main flow path 360 of the fluid. Moreover, because of the strength of sapphire or diamond, very high sealing forces may be applied to such a window 316 allowing hermetic sealing of the fluid flow path 360 from the other components (e.g., electronics) such that DO sensor 300 may be suitable for higher pressure environments, allowing DO sensor 300 to be utilized even in high pressure environments that can have sealed line pressure around 80 pounds per square inch (psi). Such sealing may, for example, be accomplished using a high purity gasket inert to acidic or basic fluids. As most processes (e.g., in the semiconductor industry) do not utilize line pressures above 60 psi such embodiments may be usefully utilized in the vast majority of such processes.

Housing 302 contains optical probe 350 and main printed circuit board (PCB) 352. Optical probe 350 may be opposite window 316 from flow path 360 and generally aligned tangentially to the flow path 360 at an angle to window 316 and luminophor 316. In some embodiments optical probe 350 may generally be aligned on an axis perpendicular to window 316 and flow path. Optical probe 350, in turn, includes probe sleeve 340 with optical probe tip 354 (which may be formed integrally to probe sleeve 340 or separately from probe sleeve 340 and affixed thereto), optical reception guide 356, optical carrier 370, optical PCB 372, reference LED 376, photodiode 374, excitation LED 378 on excitation PCB 380 and optical transmission guide 358. The use of probe sleeve 340 in combination with optical carrier 370 may be effective in preventing the "slipping" of light from the LEDs 376, 378 (e.g., optical crosstalk), as will be discussed in more detail.

Excitation LED 378 has its own PCB 380 separate from optical PCB 372 to avoid optical or electrical crosstalk between excitation components on excitation PCB 380 and components, such as detection components, on the optical PCB 372. In one embodiment, to further reduce optical and electrical crosstalk, excitation PCB 380 and optical PCB 372 may be located on opposite sides of optical carrier 370 and excitation LED 378 is coupled to (e.g., through excitation PCB 380) optical PCB 372 and is configured to be controlled by electronic components 390 on optical PCB 372. In some of these embodiments, optical carrier 370 may be cylindrical in shape with optical PCB 372 and photodiode 374 on one hemisphere of the optical carrier 370 and excitation PCB 380 and excitation LED 378 on the other hemisphere of optical carrier 370.

Similarly, then, in one embodiment, optical PCB 372 is separated from, and coupled to, main PCB 352. Specifically, in some embodiments, optical PCB 372 lies within probe sleeve 340 and main PCB 352 lies outside of probe sleeve 340. Main PCB 352 may contain electronic components 386 such as voltage regulation, power and analog output components while optical PCB 372 may contain electronic components 390 such as the photodiode front end, temperature sensor front end, LED front end for excitation or reference LEDs, digital/analog converters (DAC or ADC), digital signal processors (DSPs), microcontrollers executing, for example, modules such as firmware with control or calculation modules, or storage (e.g., EEPROMs) that may include data such as calibration data or the like. While it should be noted that all components for DO sensor 300 depicted here with respect to main PCB 352, excitation PCB 380 and optical PCB 372 may be contained on a single PCB (or two PCBs, etc.), by separating these types of components onto separate PCBs (and by further separating these components by, for example, placing optical PCB 372 in sleeve 340) crosstalk from the components on main PCB 352 can prevented from affecting the measurement or other electronic components 390 on optical PCB 372.

Probe tip 354 may have an opening through which optical reception guide 356 and optical transmission guide 358 may be routed. Optical reception guide 356 may be configured to conduct light (e.g., emitted by luminophor 310) to photodiode 374. Optical reception guide 356 may be, for example, a single cylindrical polymer fiber aligned with (e.g., on axis) photodiode 374. Optical transmission guide 358 may be configured to conduct light from excitation LED 378 to the opening in the probe tip 354 to, for example, excite or otherwise illuminate luminophor 310. Optical transmission guide 358 may be, for example, a bundle of one or more fibers (which may be of smaller diameter than the optical reception guide 356). In one embodiment, optical reception guide 356 and optical transmission guide 358 may be routed through the same opening in probe tip 354 with the bundle of fibers comprising the optical transmission guide forming an illumination ring around the circumference of optical reception guide 356.

Photodiode 374 may be coupled to optical PCB 372 where electronic components 390 of optical PCB 372 may include the front end for the photodiode (e.g., the anode and cathode for the photodiode 374). In one embodiment, electronic components 390 may include an anode (or connection therefore) for photodiode 374 on one side of optical PCB 372 and a cathode (or connection therefore) for photodiode 374 on the other side of PCB 372. This arrangement may allow photodiode 374 to be mounted on axis with and in closer proximity to optical PCB 372 to reduce the overall length of the combination of optical PCB 372 and photodiode 374. Thus, in some embodiments, photodiode 374 and PCB 372 may be generally aligned on the same axis where that axis may generally be the axis of alignment of optical probe 350 itself (e.g., generally perpendicular to window 316 and flow path 360). Reference LED 376 may also be mounted on optical PCB 372 and, in one embodiment, may be mounted behind photodiode 374 (which may be at least partially transparent) to allow direct illumination of photodiode 374 (e.g., such that photodiode 374 can detect light directly emitted from reference LED 376 and that has not traveled through optical reception guide 356). Such illumination may be restricted by an aperture or by other means.

In certain embodiments, one or more optical filters or combination of optical filters may be utilized to prevent optical crosstalk and increase fluorescence detection. The number and type of filters utilized may depend on the excitation LED 378 (e.g., the color of excitation LED 378) or the chemistry of luminophor 310 (e.g., the wavelength of light emitted by luminophor 310). It will be noted that that embodiments of LEDs utilized in embodiments as disclosed here may be almost any color desired (e.g., red, blue, green, etc.). For example, in some embodiments luminophor 310 may be selected such that it radiates substantially in the red wavelengths and excitation LED 378 may be chosen such that it radiates substantially in the green wavelengths at approximately 525 nm and a luminous intensity of around 800 millicandela (mcd). In such embodiments, a green filter may be utilized in front of excitation LED 378 to ensure that only desired green wavelengths are conducted by optical transmission guide 358 to excite luminophor 310. Similarly, a red filter may be utilized between optical reception guide 356 and photodiode 374 to ensure that only red light emitted by luminophor 310 is received by photodiode 374 (e.g., through optical reception guide 356).

In operation of certain embodiments then, electronic components 390 such as a control module executing on a controller may perform a measurement cycle. In certain embodiments, the measurement cycle may be, for example, on the order of 1 second. In one embodiment, the measurement cycle includes two parts—an excitation portion and a reference portion, where in some embodiments, each portion may be approximately half the measurement cycle. It will be apparent that a measurement cycle may be longer or shorter, may comprise only one portion (e.g., an excitation portion) or portions of differing sizes, etc.

During an excitation portion of the measurement cycle, electronic components 390 may control excitation LED 378 and determine an excitation signal corresponding to the phase or magnitude of the light emitted by luminophor 310 (in contact with fluid in flow path 360) in response to illumination by excitation LED 378. Specifically, during the excitation portion electronic components 390 may operate excitation LED 378 at a certain frequency, which in one embodiment may be approximately 16 KHz. Each time excitation LED 378 is operated (e.g., illuminated) during the excitation portion the light emitted by excitation LED 378 is conducted from excitation LED 378 through optical transmission guide 358 through the opening in probe tip 354 where it illuminates luminophor 310 through optically transparent window 316. In response to this illumination, luminophor 310 emits light and is quenched based on the presence of oxygen in fluid in flow path 360. The light emitted by luminophor 310 passes through window 316 and is received at optical reception guide 356 where it is conducted to photodiode 374 which generates a signal in response to this received light.

This signal is received by electronic components 390 which generates an excitation signal based on the signal from the photodiode 374. This excitation signal corresponds, for example, to the magnitude or phase of the light received through photodiode 374 as emitted by luminophor 310. In such an embodiment a final excitation signal may be determined using the excitation signals generated each time the excitation LED 378 is operated during the excitation portion of the measurement cycle. This final excitation signal may, for example, be an average of the excitation signals generation each time excitation LED 378 is operated during the excitation portion.

In addition, in one embodiment, during the excitation portion, electronic components 390 may receive one or more signals from temperature sensor 312. This received signal may be processed by electronic components 390 (e.g., using modulation, a peak detector, etc.) to determine a measure of temperature for fluid in flow path 360. It will be noted that the measure of temperature may be determined at any point during measurement cycle.

During the reference portion of the measurement cycle, then, electronic components 390 may operate reference LED 376 at a certain frequency, which in one embodiment may be the same frequency at which excitation LED 378 was operated in the measurement portion and may be approximately 16 KHz. Each time reference LED 376 is operated (e.g., illuminated) during the reference portion the light emitted by reference LED 376 may be received directly by photodiode 374 (e.g., through the rear of photodiode 374 mounted in proximity to optical PCB 372) which generates a signal in response to this received light.

This signal is received by electronic components 390 which generates a reference signal based on the signal from the photodiode 374. This reference signal corresponds, for example, to the magnitude or phase of the light received through photodiode 374 as emitted by reference LED 376. In such an embodiment a final reference signal may be determined using the reference signals generated each time the reference LED 376 is operated during the reference portion of the measurement cycle. This final reference signal may, for example, be an average of the reference signals generation each time reference LED 376 is operated during the reference portion.

Electronic components 390 then uses the excitation signal generated during the excitation portion of the measurement cycle to generate a signal indicating a measurement of the oxygen concentration of the fluid in flow path 360. Specifically, the decay time of the light emitted by the luminophor 310 may have an inverse and linear relationship to the dissolved oxygen concentration in the fluid. Thus, the excitation signal may be used to derive a decay time or decay time constant corresponding to the decrease in fluorescence as dissolved oxygen in the fluid interacts with the fluorescing material of luminophor 310 to quench or decrease the amount of fluorescence of that material.

In particular, in certain embodiments, the phase of the excitation signal may be determined. Additionally, a delay in sensor electronics such as those on optical PCB 372 may be accounted for using the reference signal (e.g., the phase of the reference signal) determined during the reference portion of the measurement cycle. As electronic components 390 are responsible for generating the signal for modulating reference LED 376 (e.g., at 16 KHz) and receives a signal from photodiode 374 when light from the reference LED 376 is received at photodiode 374, the difference between the phase of the excitation signal and the reference signal is associated with the delay in electronic (and possibly other) components 390 or temperature sensitivities, etc. of DO sensor 300. Thus, the reference signal (e.g., the phase of the reference signal) may be used to adjust the excitation signal to remove any phase shift in the excitation signal due to, for example, the delay in electronic components 390 or temperature sensitivities or the like. The corrected phase of the excitation signal can be used to accurately determine the decay time of the fluorescence of luminophor 310 during the excitation portion (e.g., by determining a phase difference between the modulation signal during the excitation portion of the measurement cycle and the excitation signal (e.g., the final excitation signal)). A measure of concentration of the oxygen in the fluid can then be determined based on relationship between the known decay time constant of luminophor 310 and the determined decay time. This measure may be determined, for example, using calibration data for the sensor as stored in electronic components 390 (e.g., in an EEPROM or the like).

In some embodiments, this measure of concentration can be further adjusted using the temperature value determined during the excitation portion or otherwise during the measurement cycle using a known relationship between temperature and oxygen concentration in the liquid. Correction using a measure temperature value may allow substantially real-time compensation for fluid temperature transients or steady state changes. The measure may be compensated using temperature calibration data stored in electronic components 390 (e.g., in an EEPROM or the like), where the calibration data includes zero point calibration data obtained at one temperature in the presence of no oxygen (e.g., in pure nitrogen) and at atmosphere.

Additionally, electronic components 390 may determine an alarm state during a measurement cycle indicative of the state of luminophor 310. Here, calibration data in electronic components 390 may include a nominal magnitude of fluorescence for luminophor 310. This nominal magnitude may be determined during a calibration of DO sensor 300 (e.g., when calibrating DO sensor 300 in the presence of atmosphere), may be an absolute value desired for the magnitude or may otherwise be determined. Electronic components 390 can compare the magnitude of the excitation signal generated during the excitation portion with the nominal magnitude of florescence determined during calibration and determine if the magnitude of the excitation signal is within, or outside of, some threshold (e.g., 50%, 20%, etc.) of the nominal magnitude determined during calibration. This threshold may be, for example, user configurable during calibration. If the magnitude of the excitation signal is outside of some threshold of the nominal magnitude an alarm flag may be set indicating the luminophor 310 needs replacement. It will be noted that in some instances, the alarm state may not be determined every measurement cycle, or may only be determined when specified by a process controller or the like.

Electronic components 390 may then provide signals indicative of a measure of oxygen concentration, temperature or the alarm state to main PCB 352. Electronic components 388 of main PCB 352 in turn provides corresponding signals for oxygen concentration, temperature, or alarm state (which may be in the same format, such as analog or digital, or a different format, scaled differently, etc.) through connector 308.

Figure 4A:
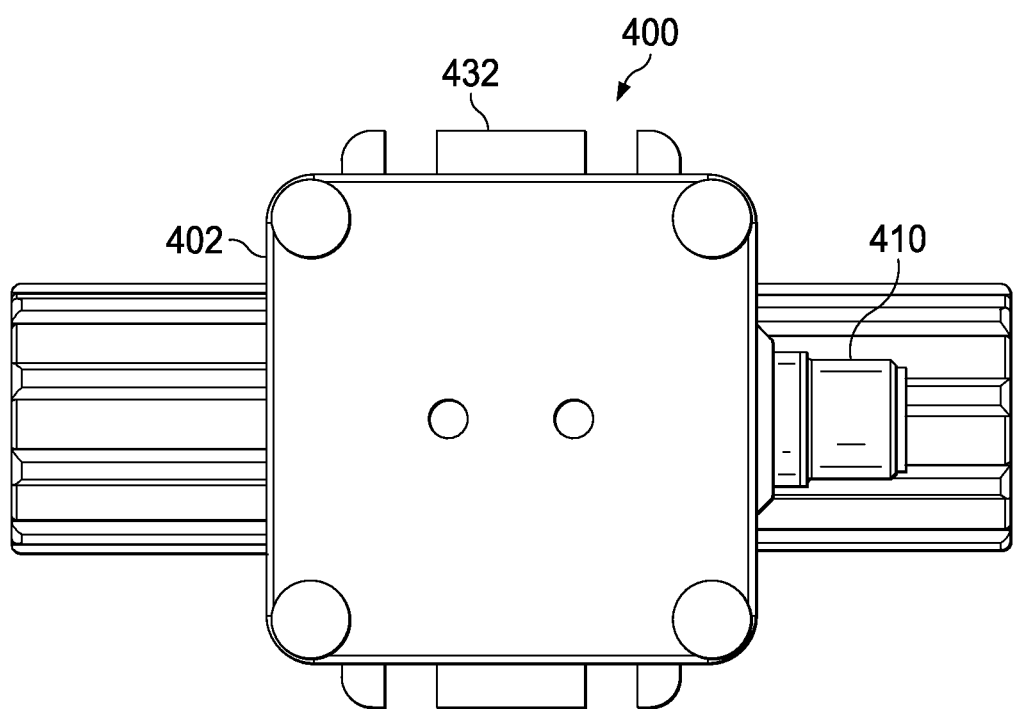
FIGS. 4A-4C is diagrammatic representations of a DO sensor.
Figure 4B:
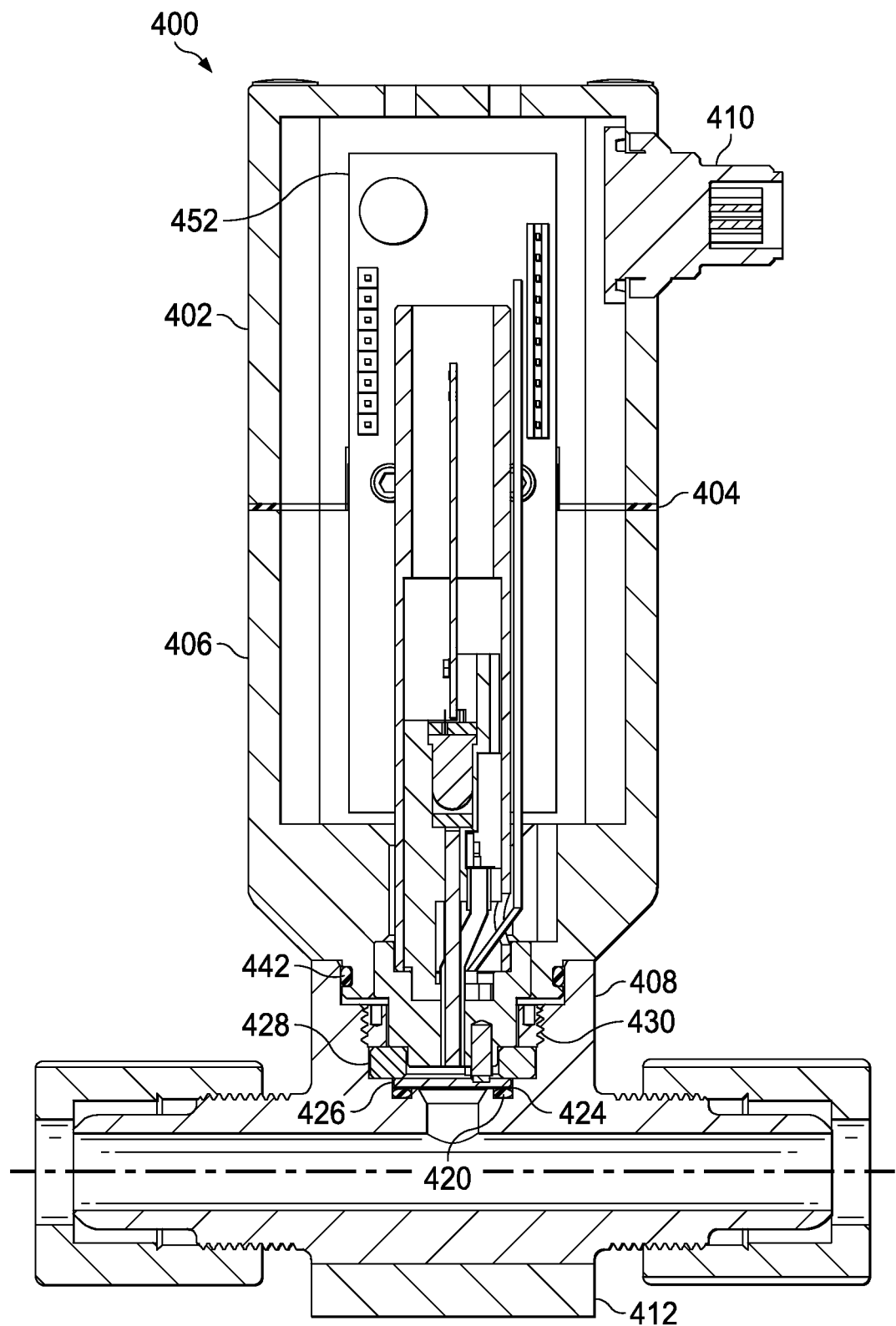
Figure 4C:
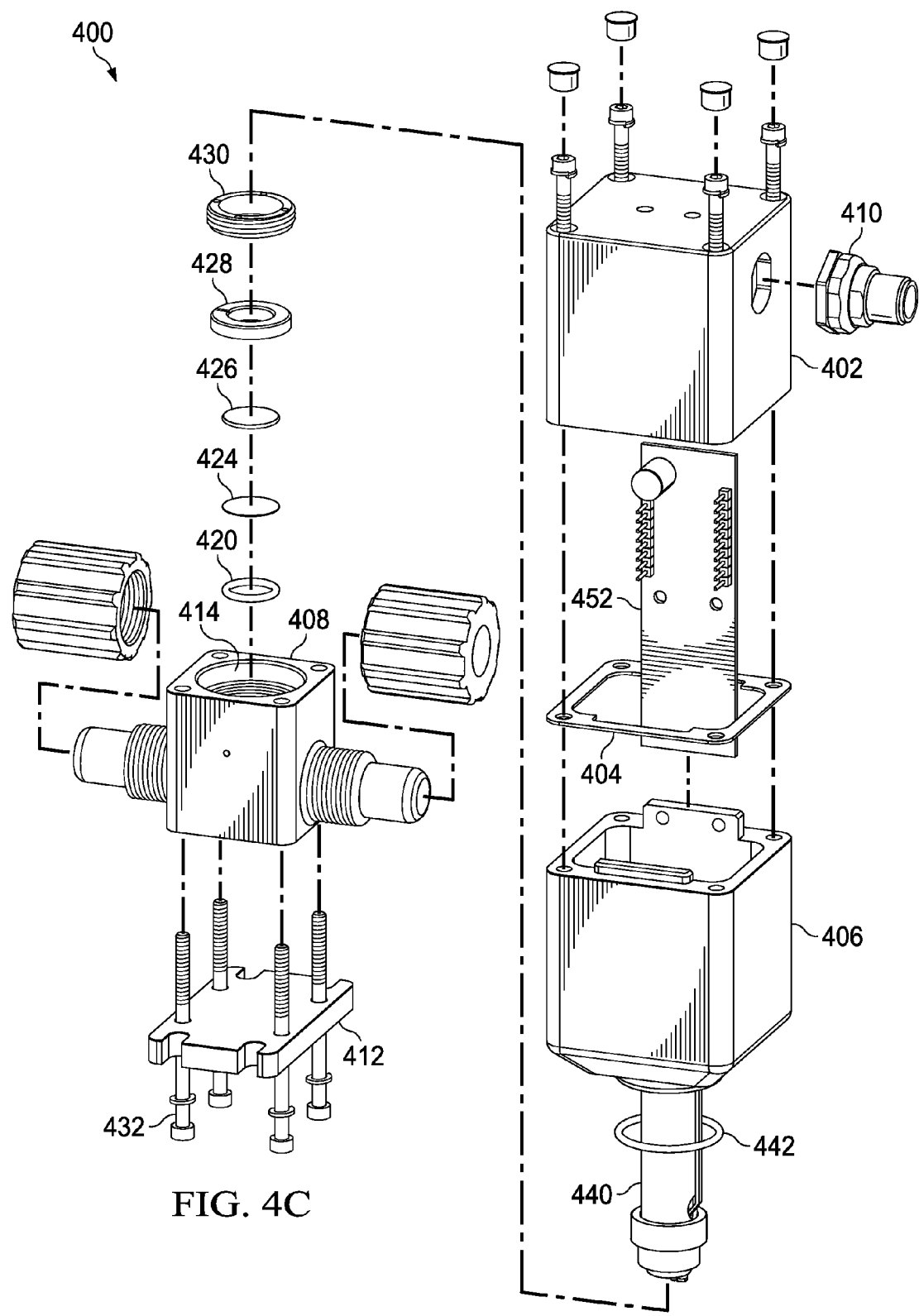

FIGS. 4A-4C depict an exploded view of one embodiments of a DO sensor such as those described above. It will be apparent that the components depicted are provided by way of example, other embodiments may or may not use each component depicted, or may use lesser or fewer components, may combine functionality of components, etc. DO sensor 400 includes upper housing 402 which may be made of plastic or the like and lower housing 406 which may be made of the same or similar material to upper housing 402. Gasket 404 may be used between upper housing 402 and lower housing 406 which may be joined together using screws and washers or the like. Additionally, connector 410 such as a Turck 12 pin connector of the like may be joined to upper housing 402. Main PCB 452 may reside at least in part in upper housing 402 such that wires may be run from main PCB 452 to connector 410 through upper housing 402.

Flow path body 408 containing the fluid flow path as described above may be made of PTFE or a similar SEMI 57 compliant material and may have a mounting plate 412 joined to the bottom of the body 408 using, for example screws 432 and washers. Top of flow path body 408 may have an opening 414 to the flow path within flow path body 408.

Optical probe 440 may be retained at least partially in lower housing 406 and lower housing 406 joined to flow path body 408 such that the tip of optical probe 440 is a working distance from optical window 426 sealed in the opening 414 to the flow path within flow path body 408. This working distance may be an air gap between the tip of the optical probe and the optical window 426 to allow light travelling through optical window to be received through the tip of the optical probe 440. In one embodiment, such a working distance may be, for example, around 0.045". Specifically, o-ring 420, luminophor 424, window 426 (e.g., sapphire or the like), retainer 428 and retainer nut 430 which may be made out of PVDF or the like and o-ring 442 which may be made of Viton or the like may be used in joining lower housing 406 to flow path body 408.

In one embodiment, flow path body 408 may have a ledge around opening 414 to the flow path configured to accept annular o-ring 420. Luminophor 424 may be adhered to window 426 and the combination sealed utilizing retainer 428 and retainer nut 430 such that luminophor 424 will be in contact with fluid in the flow path of flow path body 408. In one embodiment, both the circumference of flow path body 408 near opening 414 and the retainer nut 430 may be threaded such that a desired sealing force can be applied to window 426 by tightening or torqueing retainer nut 430 to a desired pressure.

Both retainer 428 and retainer nut 430 may be annular such that tip of optical probe 440 can be placed a desired working distance from optically transparent window 426. In some embodiments, retainer 428 may be of a lesser inner circumference than retainer nut 430 such that retainer 428 may provide a shelf on which portion of tip of optical probe 440 can be retained or otherwise contact. Lower body 406 of housing may be sealed to flow path body 408 using o-ring 442. Specifically, in certain embodiments lower housing 406 may be joined to flow path body 408 using the same screws 432 that fasten mounting plate 412 to flow path body 408 such that a desired sealing force may be applied on o-ring 442 between flow path body 408 and lower body 406 by tightening or torqueing screws 432 to a desired value. In other words, in some embodiments flow path body 408 may have through holes for screws 432 while lower housing 406 may have threaded holes for receiving screws 432.

The use of retainer 428 and retainer nut 430 and a separate window 426 and luminophor 424 may have many advantages with respect to maintenance or serviceability. Specifically, as has been discussed, luminophor 424 may degrade with time and exposure to oxygen in the fluid flowing through the flow path of flow path body 408. In fact, the greater the concentration of oxygen in such fluids the faster the rate of degradation. Thus, it is usually the case that luminophor 426 needs to be replaced every one to two years or so to ensure proper operation of the DO sensor.

In the past there were at least two main impediments to replacement of this luminophor. The first being that it was very difficult to determine when the luminophor should be replaced. As has been, and will be further, discussed, embodiments of a DO sensor as disclosed may provide an alarm signal indicating when the luminophor should be replaced. By accurately informing operators of a process when luminophor needs replacement accuracy of processes may be maintained and costly waste avoided.

The other main impediment was replaceability of the luminophor itself. In many cases, the luminophor was not replaceable at all, as it was affixed to a permanent party of the DO sensor. Moreover, even in cases where it was replaceable, it could not be done in easy and straightforward manner. Here, the use of retainer 428 and retainer nut 430 and a separate window 426 and luminophor 424 allow field serviceability of a DO sensor by allowing easy replacement of window 426 or luminophor 424 (which, in one embodiment may be replaced as a unit or simultaneously), while still allowing adequate sealing force to be placed in window to prevent fluid leakage and remain SEMI 57 or IP 67 compliant. In particular, lower housing 406 may be easily separated from flow path body 408 and retainer nut 430 easily removed (e.g., using a wrench or the like) to allow access to, and replacement of, window 426 or luminophor 424 (or, as mentioned, both as a unit). By reducing time of replacement, and allowing field servicing of DO sensor process downtime is significantly reduced.

Figure 5:
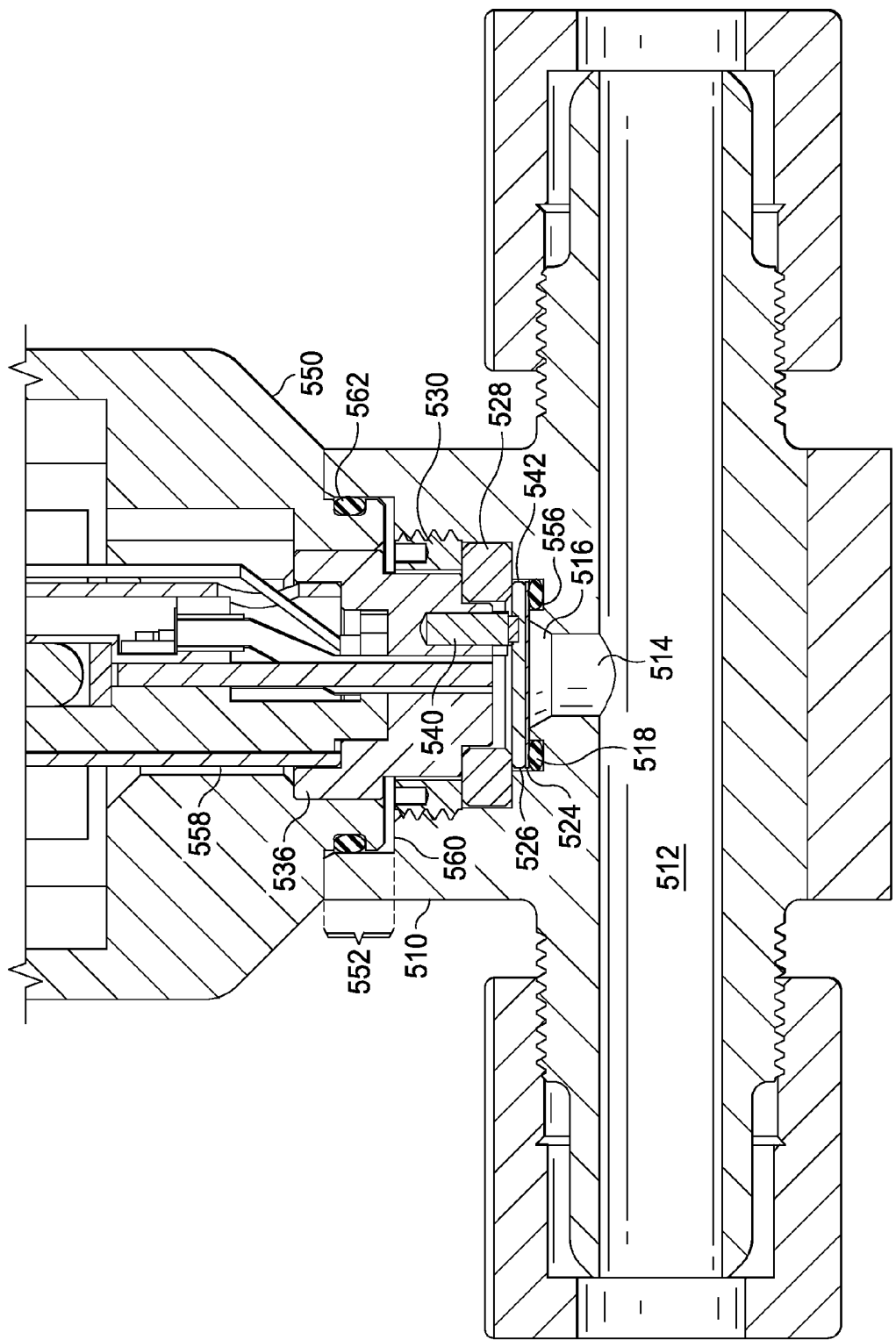
FIG. 5 is a diagrammatic representation of a portion of one embodiment of a DO sensor.

Moving now to FIG. 5, a close up cross sectional view of one embodiment of the interface between a lower housing and a flow path body of an embodiment of a DO sensor is depicted. Again, it will be apparent that the components depicted are provided by way of example, other embodiments may or may not use each component depicted, or may use lesser or fewer components, may combine functionality of components, etc. In particular, lower housing 550 includes a lower portion 552 (which may, for example, be circular in shape) adapted to fit within an opening in flow path body 510. This opening may have a lip 560 (that may be annular around the opening) such that lower portion 552 of lower housing 550 and lip 560 are adapted to contact one another. O-ring 562 may serve to seal the interface between lower portion 552 of lower housing and flow path body 510.

Flow path body 510 contains fluid flow path 512 as described above. Fluid flow path 512 includes a "T" (also referred to as a bowl) 514 to allow fluid in flow path 512 to be exposed to opening 516 in flow path body 510. 516 of around 0.25" in circumference and a depth of 0.2". Flow path body 510 includes an annular channel 556 around opening 516, where the bottom of the channel is below the top of bowl 514. O-ring 518 may reside in channel 516 such that in an uncompressed state the top of the o-ring 518 may be above, or even with the portion of flow path body 512 comprising the inner wall of the channel 516. Luminophor 524 may be adhered to window 526 and the combination placed in opening 516 and sealed utilizing retainer 528 and retainer nut 530 such that luminophor 524 will be in contact with fluid in the flow path 512 in opening 516 of bowl 514. Specifically, a portion of inner wall of flow path body 510 above opening 516 is threaded as is the outer circumference of retainer nut 530. Retainer nut 530 can thus be tightened to place a desired sealing force on luminophor 524 through retainer 528. This sealing force serves to compress o-ring 518 and provide a hermetic seal such that liquid (or molecules thereof) cannot escape fluid flow path 512.

Tip 536 of optical probe 558 may be stepped such that portions of tip may have different circumferences. One step of tip 536 may contact against retainer 528 such that it resides a working distance from window 526 while another step of tip 536 may contact retainer nut 530. In one embodiment, tip 536 includes a receptacle for a compressor 540 (e.g., made from silicon, rubber or the like) such that compressor 540 may compress temperature sensor 542 adhered to window 526 opposite the fluid flow path 512. Tip 536 may also have one or more holes (not shown) for routing of wires from temperature sensor 542 to electronic components of the optical probe 558. Ends of an optical transmission guide and an optical reception guide may be routed through an opening in the tip 536. In one embodiment, the optical transmission guide or optical reception guide may be contained by an optical sleeve in the tip surrounding the optical transmission guide or optical reception guide.

Figure 6A:
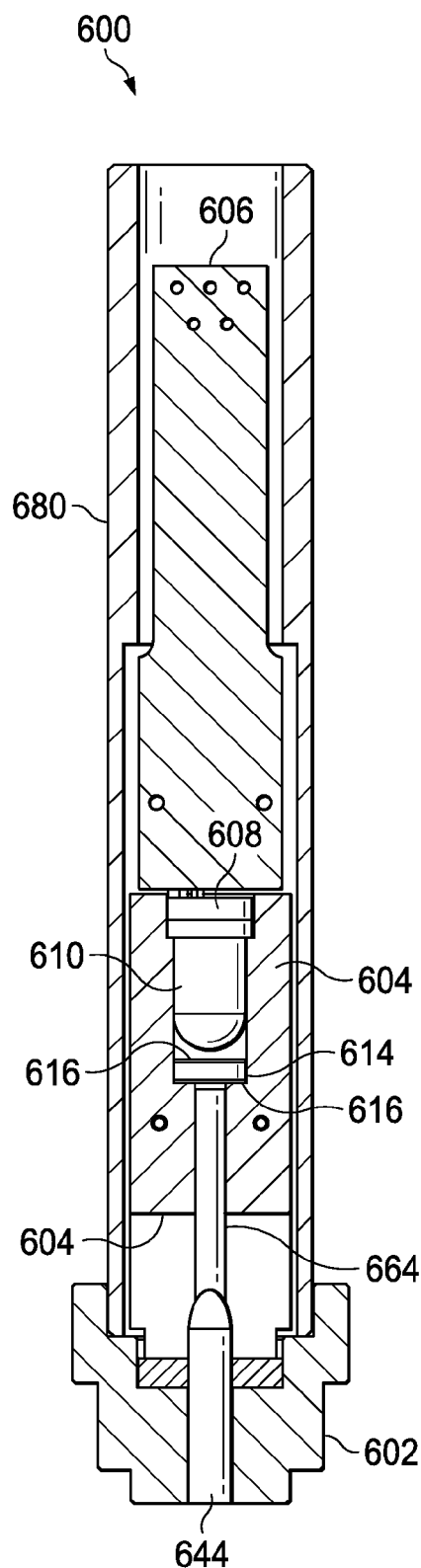
FIGS. 6A-6C are a diagrammatic representation of one embodiment of an optical probe for use with embodiments of a DO sensor.
Figure 6B:
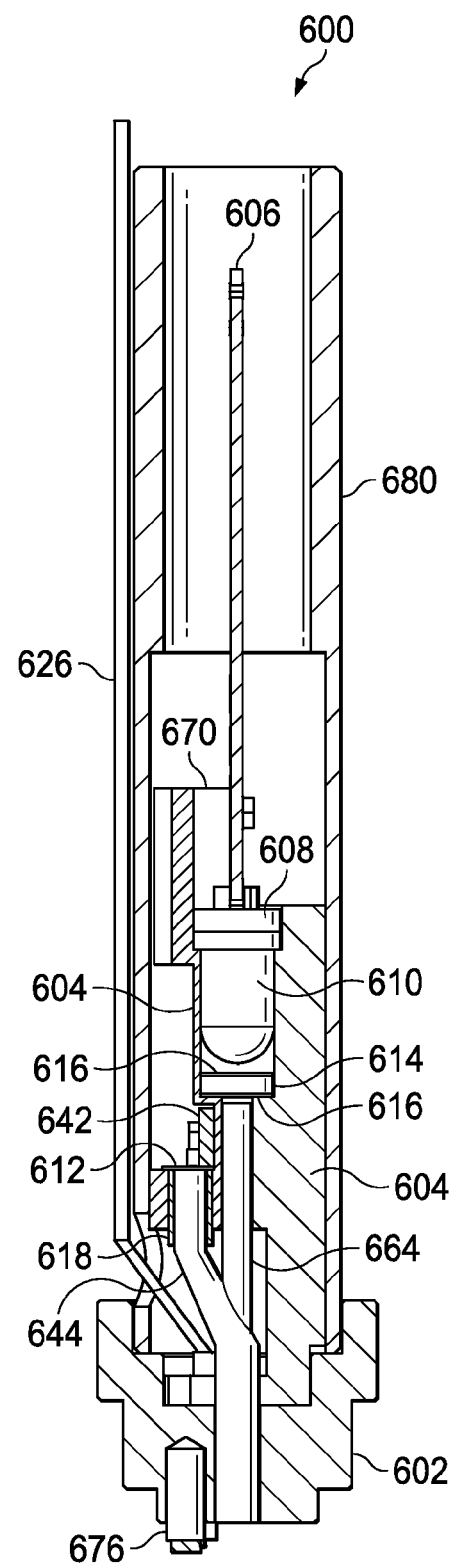
Figure 6C:
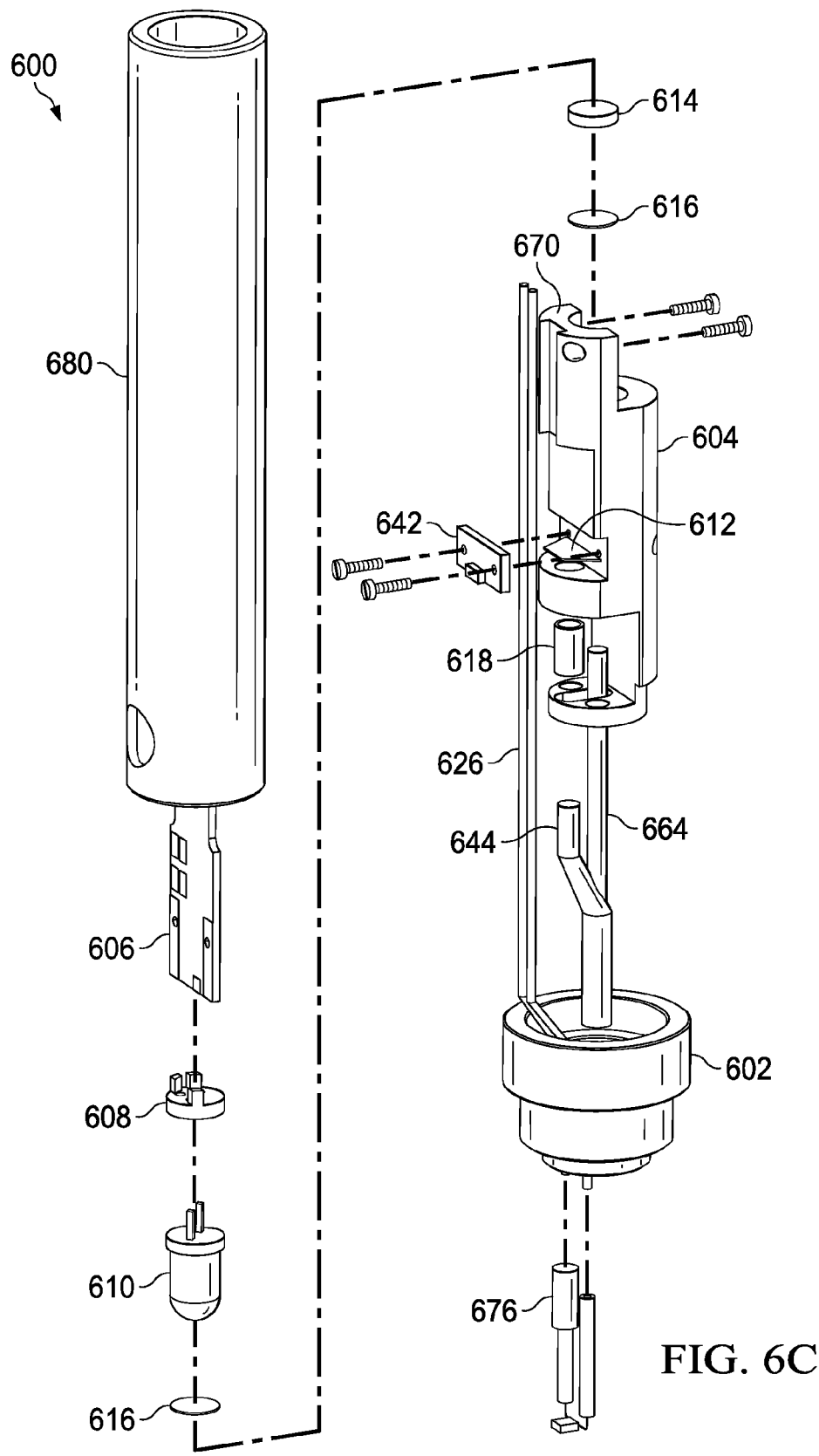

Turning now to FIGS. 6A-6C, an exploded view of one embodiments of an optical probe that may be utilized in a DO sensor such as those described above is depicted. As with the other embodiments depicted herein, it will be apparent that the components depicted are provided by way of example, other embodiments may or may not use each component depicted, or may use lesser or fewer components, may combine functionality of components, etc. Optical probe 600 includes sleeve 680 joined to probe tip 602. Optical carrier 604 resides within sleeve 680. Optical carrier 604 is generally cylindrical. On one side or hemisphere of optical carrier 604 there is an indentation adapted to receive excitation PCB 642 including excitation LED. The excitation PCB 642 may be affixed to optical carrier 604 using, for example, screws, adhesive or another fastener. Optical transmission guide 644 may be placed within optical transmission sleeve 618 and routed through a generally circular opening in the center of probe tip 602. Optical filter 612 (e.g., a green filter or the like as described earlier) may be affixed to optical carrier 604 between excitation LED on excitation PCB 642 and optical sleeve 618. This side of optical carrier 604 may also have a channel for routing of wires 626, from for example, the excitation PCB 642 to optical PCB 606 or temperature sensor (not shown) to optical PCB 606. Portion 670 of this side of optical carrier 604 may form a barrier that serves as a divider and a mounting point for optical PCB 606. This portion 670 may be a wall around a portion of circumference of optical carrier 604.

The other side of optical carrier 604 has a cylindrical bore through the optical carrier 604 such that optical reception guide 664 is routed through this cylindrical bore and through the opening in the center of probe tip 602. In certain embodiments, a portion of optical reception guide not within the cylindrical bore may be encased in an optical sleeve. As discussed above, in some embodiment, optical transmission guide 644 and optical reception guide 664 may be routed through the same hole in probe tip 602 with optical transmission guide 644 wrapping around optical reception guide 664 to form an illumination ring or the like. Optical reception guide 664 may for example, be a single 2 mm in diameter fiber optic while optical transmission guide 644 may be a bundle (e.g., 10-15) of 0.5 mm in diameter fibers.

Photodiode 610 is mounted to optical PCB 606 including reference LED by routing the anode and cathode of photodiode 610 through one or more holes in optical diaphragm 608. Optical diaphragm 608 may also include a hole through which light emitted by reference LED on optical PCB 606 may directly illuminate photodiode 610. Such a hole may also serve to aperture restrict such illumination. Optical PCB 606 may be affixed to portion 670 of optical carrier 604 such that photodiode 610 may be positioned in cylindrical bore of optical carrier 604. In one embodiment, filters 616 on either side of hot mirror 614 may be positioned in the cylindrical bore between photodiode 610 and end of optical reception guide 664 distal from the opening in probe tip 602.

Optical carrier 604 including optical PCB 606, excitation PCB 642 and all components mounted on, or otherwise routed through optical carrier 604 may be placed in probe sleeve 680 and probe tip 602 may be affixed to the end of probe sleeve 680, for example, using adhesive or the like. Additionally, compressor 676 for compression of a temperature sensor may be affixed in a receptacle in probe tip 602.

It may now be useful to look at more specific embodiments of certain components of embodiments of a DO sensor as have been discussed. The embodiments of the components depicted in FIG. 7-10 may be sized appropriately to fit in a DO sensor (e.g., a combination of an upper housing, lower housing and flow path body) approximately 5.75" in height (e.g., for the combination of an upper housing, lower housing and flow path body) and with a housing (e.g., an upper and lower housing) measuring approximately 1.75". It will be apparent that all dimensions are approximate and are applicable only to that particular embodiment. Other embodiments may be use the same component with different dimensions, may not use such a component, or may lesser or fewer components, etc.

Figure 7A:
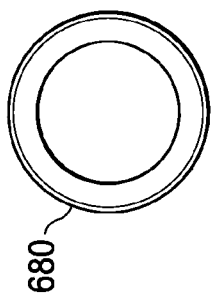
FIGS. 7A-7C are a diagrammatic representation of one embodiment of an optical sleeve for use with embodiments of a DO sensor.
Figure 7B:
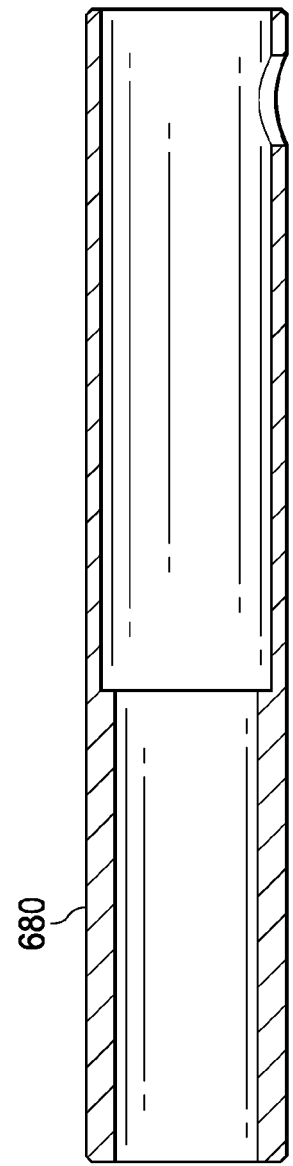
Figure 7C:
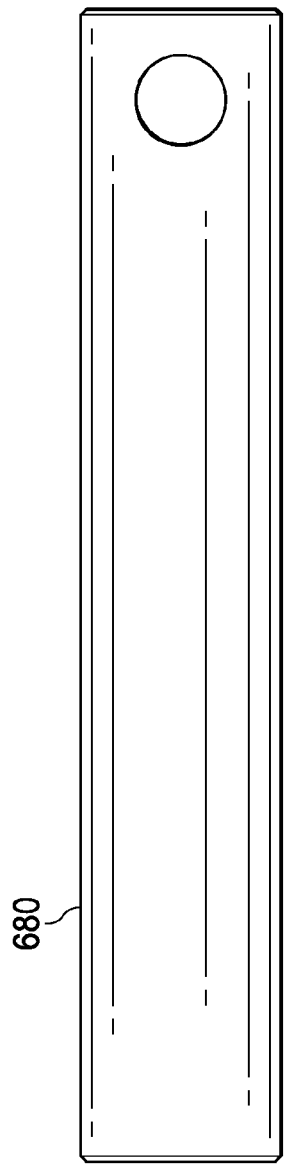
Figure 8A:
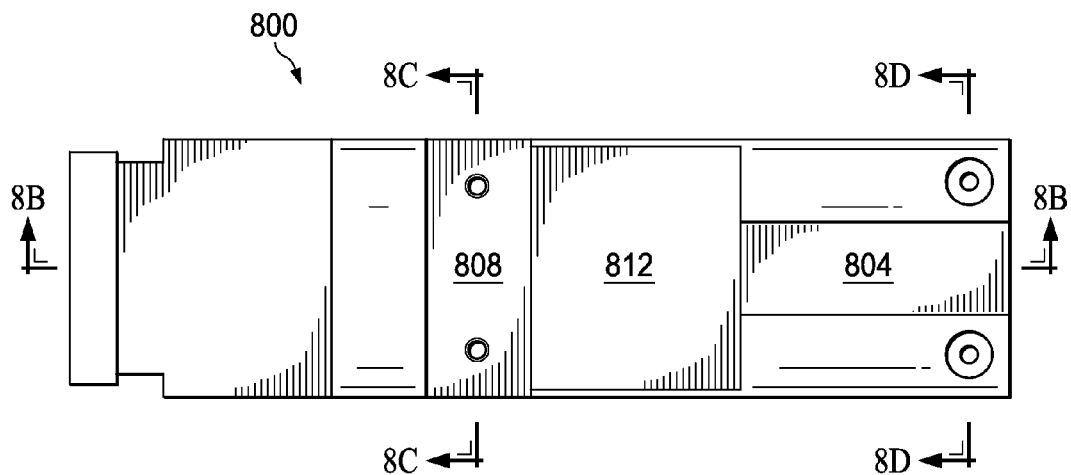
FIGS. 8A-8H are a diagrammatic representation of one embodiment of an optical carrier for use with embodiments of a DO sensor.
Figure 8B:
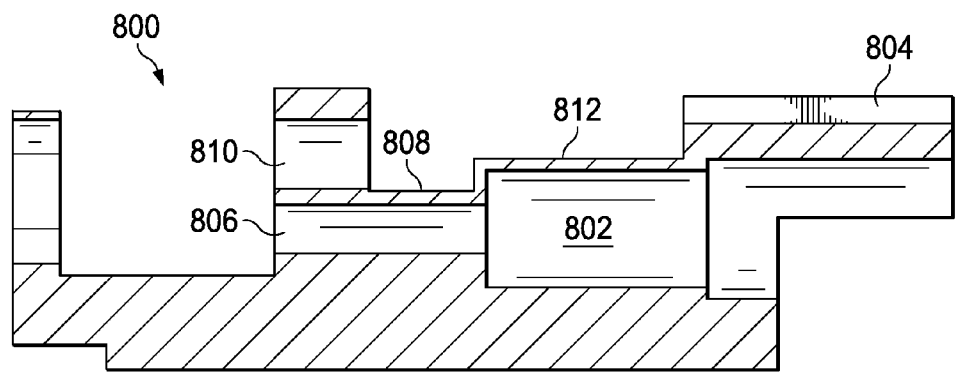
Figure 8C:
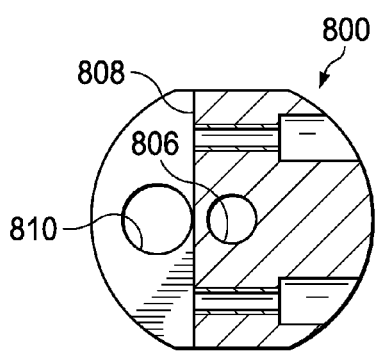
Figure 8D:
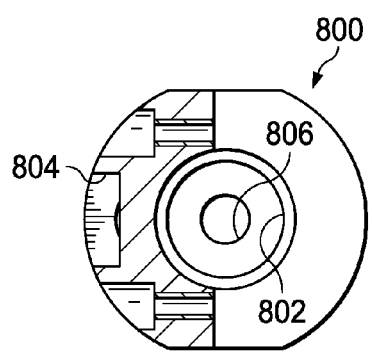
Figure 8E:
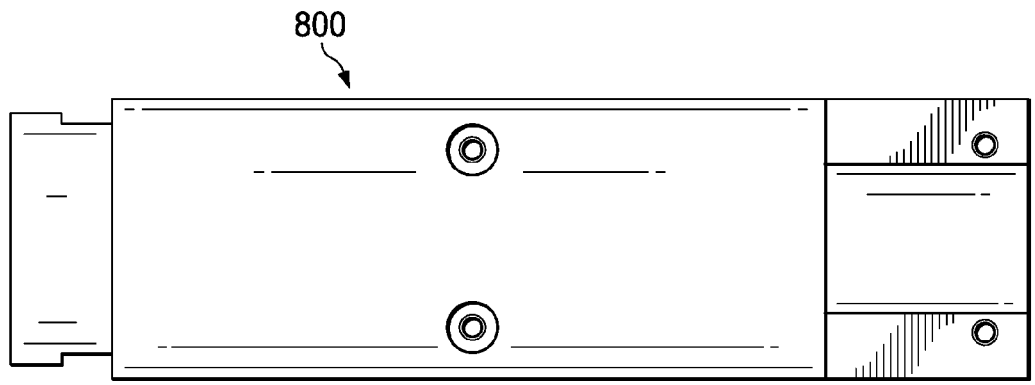
Figure 8F:
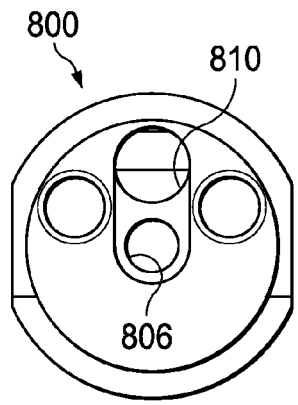
Figure 8G:
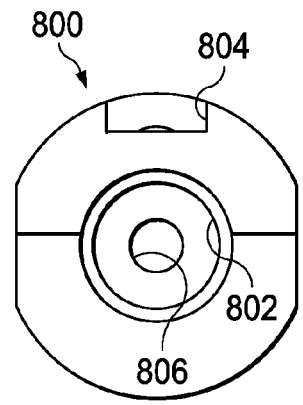
Figure 8H:
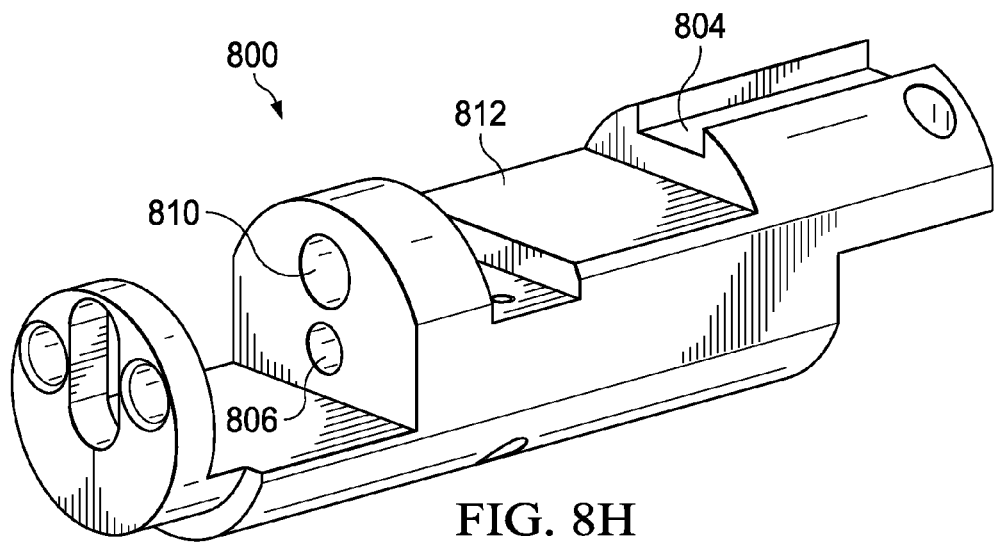

With that in mind, FIGS. 7A-7C depict one embodiments of a sleeve for an optical probe for use with a DO sensor while FIGS. 8A-8H depict one embodiment of an optical carrier for use with the sleeve of FIGS. 7A-7C. Notice here, that optical carrier 800 includes, chamber 802 where a photodiode mounted on an optical PCB may reside when the optical PCB is affixed to portion 804 of optical carrier 800. In such an arrangement, bore 806 may accommodate an optical reception guide or portion thereof such that an end of the optical reception guide distal a window of the DO sensor may be proximate the photodiode in chamber 802. Recess 808 may be designed to accommodate an excitation PCB such the excitation LED illuminates an optical transmission guide contained in bore 810. As wall 812 of optical carrier 800 separates the optical PCB, photodiode and optical reception guide from excitation PCB, excitation LED and optical transmission guide the optical carrier 800 serves to significantly reduce both optical electrical crosstalk in DO sensors that utilize such an optical carrier.

Figure 9:
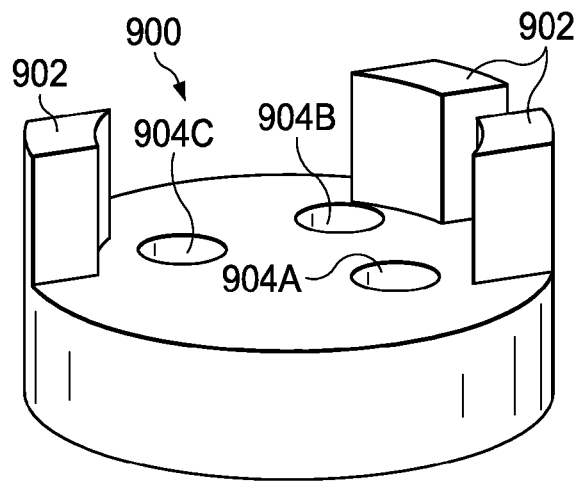
FIG. 9 is a diagrammatic representation of one embodiment of an optical diaphragm for use with embodiments of a DO sensor.

FIG. 9 depicts an embodiment of a optical diaphragm 900 that may be utilized between a photodiode and an optical PCB. Notice here that optical diaphragm contains three prongs 902 for retaining an optical PCB and three through holes 904. Two through holes 904a, 904b may be for routing of anode and cathode of a photodiode such that they may be soldered or otherwise attached to opposite side of an optical PCB retained by prongs 902. The third through hole 904c may allow a reference LED mounted on an optical PCB to which the photodiode is soldered to illuminate the photodiode from the rear, and may additionally provide restriction on such illumination.

Figure 10A:
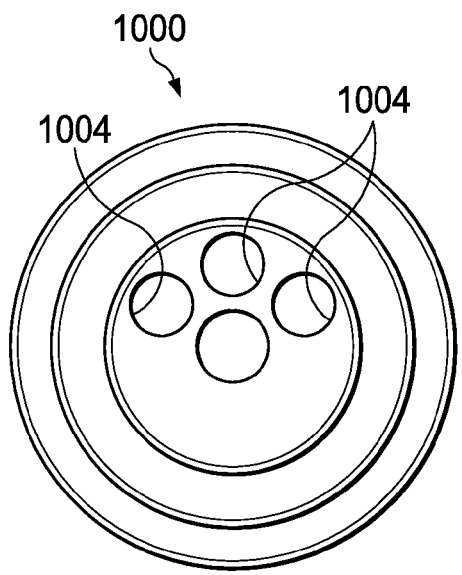
FIGS. 10A and 10B are a diagrammatic representation of one embodiment of a probe tip for use with embodiments of a DO sensor.
Figure 10B:
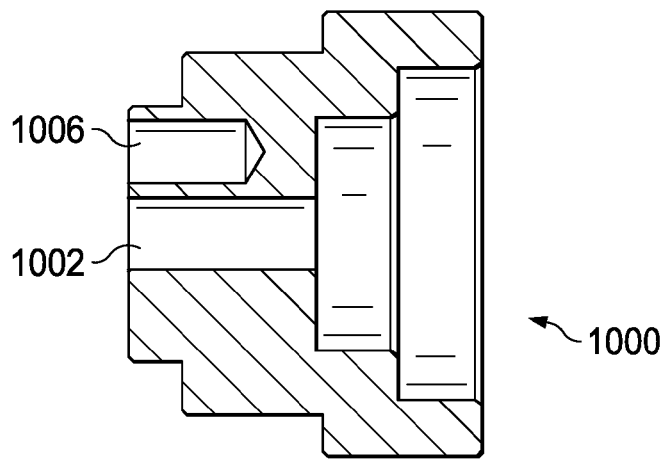

FIGS. 10A and 10B depict one embodiment of a probe tip 1000. Notice here that probe tip 1000 has through hole 1002 through which an optical transmission guide and optical reception guide may be routed. Probe tip 1000 may also have one or more through holes 1004 through which wires from a temperature sensor adhered to a window of DO sensor may be routed. Additionally, probe tip 1000 may have a recess 1006 where a compressor (e.g., made of rubber or silicon) may be located to compress the temperature sensor adhered to the window.

It may now be helpful to an understanding of embodiments as depicted herein to discuss methods of calibrating or operating embodiments of DO sensors such as those depicted herein. Such methods may be performed using electronic components (e.g., hardware, software or some combination) of DO sensor as discussed above. FIG. 11 depicts an embodiment of calibration for DO sensor. At step 1110 a zero calibration may be performed. In such a calibration the sensor may be calibrated in an environment with substantially zero oxygen by for example, by calibrating the DO sensor in a pure nitrogen environment. The zero point calibration may be done at a known temperature value and is used to determine, adjust or set output values associated with the sensor in such an environment.

At step 1120 a 100% calibration may be performed. In this step the temperature may be held at the known temperature value and the sensor exposed to atmosphere. In some embodiments, the DO sensor may be exposed to atmosphere for at least 30 minutes to allow a stable oxygen level to be established. The 100% calibration done at the known temperature value and is used to determine, adjust or set output values associated with the sensor in such an environment. For example, such a calibration may allow a temperature measured during a measurement cycle to be used to compensate or otherwise adjust a measurement of oxygen concentration based on a relationship between temperature and oxygen concentration.

Additionally, in certain embodiments, during the 100% calibration a magnitude of fluorescence value for the luminophor of the DO sensor may be determined. This magnitude of fluorescence value may, for example, be a maximum value of the intensity of light received from luminophor during the calibration process or an average of the maximum intensity of light received from luminophor over multiple illuminations of luminophor, etc. This magnitude of fluorescence value may be stored in the DO sensor (e.g., in an EEPROM or the like).

It may also be possible, in one embodiment, to calibrate the DO sensor in the presence of a fluid with which it will be utilized (e.g., in an installation in a semiconductor process, etc.). Thus, a magnitude of fluorescence value may, in some embodiments, be determined by performing a calibration of DO sensor in the presence of a particular fluid and a magnitude of fluorescence value determined with respect to that particular process fluid.

FIG. 12 depicts an embodiment of a method for performing determining an oxygen concentration of a fluid in a flow path as may be performed by embodiments of a DO sensor as discussed herein. A measurement cycle may include an excitation portion 1210 and a reference portion 1250. In certain embodiments, the measurement cycle may be, for example, on the order of 1 second, where in some embodiments, each portion may be approximately half the measurement cycle. It will be apparent that a measurement cycle may be longer or shorter, may comprise only one portion (e.g., an excitation portion) or portions of differing sizes, etc.

During an excitation portion 1210 of the measurement cycle, at step 1212 an excitation LED is operated. In one embodiment, excitation LED is operated (e.g., turned on and off or pulsed) at a certain frequency, which in one embodiment may be approximately 16 KHz. Each time excitation LED is operated (e.g., illuminated) during the excitation portion 1210 the light emitted by excitation LED is conducted from excitation LED through optical transmission guide through the opening in probe tip where it illuminates the luminophor of the DO sensor. In response to this illumination, luminophor emits light and is quenched based on the presence of oxygen in fluid in the flow path. The light emitted by luminophor is received, at step 1214, by the photodiode which generates a signal in response to this received light. An excitation signal is then generated at step 1216 based on the signal from the photodiode. This excitation signal corresponds, for example, to the magnitude or phase of the light received through the photodiode as emitted by the luminophor. A final excitation signal may be determined at step 1218 using the excitation signals generated each time the excitation LED is operated during the excitation portion 1210 of the measurement cycle. This final excitation signal may, for example, be an average of the excitation signals generated (at step 1216) each time excitation LED is operated during the excitation portion 1210 of the measurement cycle.

During the reference portion 1250 of the measurement cycle, then, reference LED may be operated at step 1252 at a certain frequency, which in one embodiment may the same frequency at which excitation LED was operated in the excitation portion 1210 and may be approximately 16 KHz. Each time the reference LED is operated (e.g., illuminated) during the reference portion 1250 the light emitted by reference LED may be received, at step 1254, directly by photodiode which generates a signal in response to this received light.

At step 1256 a reference signal is generated based on the signal from the photodiode. This reference signal corresponds, for example, to the magnitude or phase of the light received through photodiodes emitted by reference LED. A final reference signal may be determined at step 1258 using the reference signals generated each time the reference LED is operated during the reference portion 1250 of the reference portion. This final reference signal may, for example, be an average of the reference signals generation each time reference LED is operated.

In addition, at step 1260 at some point during the measurement cycle (which may be during the excitation portion the reference portion, between the portions, after the portions, an average of multiple temperature measurements taken during multiple points during the measurement cycle, etc.), a temperature of the fluid in the flow path of the DO sensor is determined based on a signal received from a temperature sensor.

A measure of the concentration of oxygen in the fluid may be determined at step 1270 based on the final excitation signal, the final reference signal and the temperature. Specifically, the final excitation signal may be used to derive a decay time or decay time constant corresponding to the decrease in fluorescence as dissolved oxygen in the fluid interacts with the fluorescing material of luminophor to quench or decrease the amount of fluorescence of that material. In particular, the phase of the final excitation signal may be determined and the delay in sensor electronics may be accounted for using the final reference signal (e.g., the phase of the final reference signal) determined during the reference portion of the measurement cycle. The corrected phase of the final excitation signal can be used to accurately determine the decay time of the fluorescence of luminophor during the excitation portion. The measure of concentration of the oxygen in the fluid can then be determined based on the relationship between the known decay time constant of the luminophor being utilized and the determined decay time. This measure may be determine, for example, using stored calibration data (e.g., as determined in a calibration process). This measure of concentration can be further adjusted using the temperature value determined (e.g., at step 1260) based on a known relationship between temperature and oxygen concentration.

Additionally, in some embodiments, at step 1280 an alarm state indicative of the state of luminophor may be determined during the measurement cycle. Here, calibration data in electronic components may include a reference magnitude of fluorescence for the luminophor. This reference magnitude may be a specified value, determined during the calibration of DO sensor 300, etc. This reference magnitude can be compared to the magnitude of the final excitation signal generated during the excitation portion to determine if the magnitude of the excitation signal is within some threshold (e.g., 50%, 20%, etc.) of the reference magnitude determined during calibration. This threshold may be, for example, manufacturer or user configurable during calibration. If the magnitude of the final excitation signal not within the threshold of the reference magnitude (e.g., 50% of the reference magnitude) an alarm flag may be set, or an alarm signal sent, indicating the luminophor needs replacement. It will be noted that in some instances, the alarm state may not be determined every measurement cycle, may never be determined in a measurement cycle, or may only be determined when specified by a process controller or the like.

At step 1290 then, at least a signal indicative of the measure of concentration of oxygen may be provided by the DO sensor. This signal may be used to control a process with which the DO sensor is being utilized or for a wide variety of other functions. Additionally, at step 1290, a signal indicative of a measured temperature or an alarm state may also be provided by the DO sensor.

As was briefly discussed, the alarm state may not be determined in conjunction with a measurement cycle. Thus, in some embodiments a luminophor testing cycle may be performed separately from the measurement cycle. It may be desired to perform a separate luminophor testing cycle at atmosphere, especially in cases where a reference magnitude for the luminophor was determined in a calibration process at atmosphere. Thus, before such a luminophor testing cycle is performed, the DO sensor may be brought back, or opened, to atmosphere, or may be performed during a portion of a process when atmosphere is introduced to the fluid flow path during the process, etc. It will thus be apparent that in certain embodiments such a luminophor testing cycle may be substantially identical to a measurement cycle as described above performed in the presence of atmosphere.

One embodiment of a method for performing a testing cycle to determine an alarm state for luminophor replacement is depicted in FIG. 13. In this case to perform a testing cycle the initially at step 1310 an excitation signal is generated by operating the excitation LED. It will be noted that this excitation signal may be generated substantially similarly to the other discussion of such excitation signals herein. At step 1320 an alarm state indicative of the state of luminophor may be determined. As discussed, calibration data may include a reference magnitude or the reference magnitude may have been specified in some other manner. This reference magnitude can be compared to the magnitude of the excitation signal to determine if the magnitude of the excitation signal is within some threshold of the reference magnitude determined during calibration. If the magnitude of the excitation signal is not within the threshold of the reference magnitude (e.g., 50% of the reference magnitude) an alarm flag may be set, or an alarm signal sent, at step 1330 indicating the luminophor needs replacement.

Embodiments described herein can be implemented in the form of control logic in software or hardware or a combination of both. The control logic may be stored in an information storage medium, such as a computer-readable medium, as a plurality of instructions adapted to direct an information processing device to perform a set of steps disclosed in the various embodiments. Based on the disclosure and teachings provided herein, a person of ordinary skill in the art will appreciate other ways and/or methods to implement the invention.

As used herein, the terms "comprises," "comprising," "includes," "including," "has," "having," or any other variation thereof, are intended to cover a non-exclusive inclusion. For example, a process, product, article, or apparatus that comprises a list of elements is not necessarily limited only those elements but may include other elements not expressly listed or inherent to such process, product, article, or apparatus.

A "computer-readable medium" may be any medium that can contain, store, communicate, propagate, or transport the program for use by or in connection with the instruction execution system, apparatus, system or device. The computer readable medium can be, by way of example, only but not by limitation, an electronic, magnetic, optical, electromagnetic, infrared, or semiconductor system, apparatus, system, device, propagation medium, or computer memory. Such computer-readable medium shall generally be machine readable and include software programming or code that can be human readable (e.g., source code) or machine readable (e.g., object code).

A "processor" includes any, hardware system, mechanism or component that processes data, signals or other information. A processor can include a system with a general-purpose central processing unit, multiple processing units, dedicated circuitry for achieving functionality, or other systems. Processing need not be limited to a geographic location, or have temporal limitations. For example, a processor can perform its functions in "real-time," "offline," in a "batch mode," etc. Portions of processing can be performed at different times and at different locations, by different (or the same) processing systems.

It will also be appreciated that one or more of the elements depicted in the drawings/figures can also be implemented in a more separated or integrated manner, or even removed or rendered as inoperable in certain cases, as is useful in accordance with a particular application. Additionally, any signal arrows in the drawings/figures should be considered only as exemplary, and not limiting, unless otherwise specifically noted.

Furthermore, the term "or" as used herein is generally intended to mean "and/or" unless otherwise indicated. As used herein, a term preceded by "a" or "an" (and "the" when antecedent basis is "a" or "an") includes both singular and plural of such term (i.e., that the reference "a" or "an" clearly indicates only the singular or only the plural). Also, as used in the description herein, the meaning of "in" includes "in" and "on" unless the context clearly dictates otherwise.

Benefits, other advantages, and solutions to problems have been described above with regard to specific embodiments. However, the benefits, advantages, solutions to problems, and any component(s) that may cause any benefit, advantage, or solution to occur or become more pronounced are not to be construed as a critical, required, or essential feature or component.

What is claimed is:

1. A dissolved oxygen sensor, comprising:
 a window of optically transparent material disposed in an opening in a fluid flow path, wherein a luminophor is attached to a first side of the window exposed to the fluid flow path;
 an optical probe opposite the window from the fluid flow path and the luminophor, wherein the optical probe includes:
  an excitation light source configured to illuminate the luminophor;
  an optical reception guide routed through the probe and having a longitudinal axis with a first end of the optical reception guide along the longitudinal axis proximate the window, wherein the optical reception guide is configured to conduct light received at the first end in response to illumination of the luminophor by the excitation light source;
  a photodiode configured to receive light conducted by the optical reception guide wherein the photodiode is adjacent to a second end of the optical reception guide along the longitudinal axis distal the window and is aligned on the longitudinal axis with the optical reception guide;
  a printed circuit board (PCB) having a longitudinal axis aligned with the photodiode and the longitudinal axis of the optical reception guide, wherein the photodiode is physically coupled to the PCB; and
  a reference light source configured to directly illuminate the photodiode through a portion of the photodiode proximate the PCB, wherein the PCB includes electronic components configured to determine a measure of oxygen concentration of a fluid in the fluid flow path based on the light received at the photodiode through the optical reception guide.

2. The dissolved oxygen sensor of claim 1, further comprising an optical carrier, wherein the excitation light source is on a first side of the optical carrier and the photodiode and PCB are on a second side of the optical carrier.

3. The dissolved oxygen sensor of claim 2, wherein the optical carrier includes a first chamber and the photodiode resides in the first chamber.

4. The dissolved oxygen sensor of claim 2, wherein an anode of the photodiode is coupled to a first side of the PCB and a cathode of the photodiode is coupled to a second side of the PCB.

5. The dissolved oxygen sensor of claim 2, wherein the reference light source is on the PCB.

6. The dissolved oxygen sensor of claim 5, wherein the optical carrier includes a bore having a first end open to the first chamber and a second end of the optical reception guide distal the window is within the bore.

7. The dissolved oxygen sensor of claim 6, wherein the luminophor is configured to emit red light in response to illumination by the excitation light source and a red pass filter is disposed within the first chamber between the end of the optical reception guide and the photodiode.

8. The dissolved oxygen sensor of claim 6, wherein an optical transmission guide is configured to conduct light from the excitation light source to the luminophor through an end of the optical transmission light source proximate the window.

9. The dissolved oxygen sensor of claim 8, wherein the excitation light source is configured to emit green light and a green pass filter is disposed between the excitation light source an end of the optical transmission guide distal the window.

10. The dissolved oxygen sensor of claim 9, wherein the optical transmission guide comprises a set of fibers and the end of the optical transmission guide proximate the window comprises a ring around the end of optical reception guide formed by an end of each of the set of fibers.

11. The dissolved oxygen sensor of claim 8, further comprising a flow path body including the fluid flow path.

12. The dissolved oxygen sensor of claim 11, wherein the window is sealed in the opening in the fluid flow path with a retaining nut threaded around its outer circumference and screwed into the flow path body.

13. The dissolved oxygen sensor of claim 11, wherein the retaining nut is annular and a probe tip of the optical probe is disposed within the retaining nut.

14. The dissolved oxygen sensor of claim 13, wherein the optical transmission guide and optical reception guide are routed through an opening in the probe tip.

15. The dissolved oxygen sensor of claim 13, wherein the flow path body includes an annular channel around the opening in the fluid flow path configured to receive an o-ring.

16. The dissolved oxygen sensor of claim 15, wherein the optically transparent window is sapphire.

17. The dissolved oxygen sensor of claim 1, wherein the reference light source is aligned with the photodiode along the longitudinal axis.

18. The dissolved oxygen sensor of claim 1, further comprising a temperature sensor mounted to the window opposite from the fluid flow path.

* * * * *